US012281157B2

(12) United States Patent
Cui et al.

(10) Patent No.: US 12,281,157 B2
(45) Date of Patent: Apr. 22, 2025

(54) NS1-BINDING PROTEIN

(71) Applicant: FAPON BIOTECH INC., Shenzhen (CN)

(72) Inventors: Peng Cui, Dongguan (CN); Zhiqiang He, Dongguan (CN); Yuan Meng, Dongguan (CN); Dongmei Zhong, Dongguan (CN)

(73) Assignee: Fapon Biotech Inc., Shenzhen (CN)

( * ) Notice: Subject to any disclaimer, the term of this patent is extended or adjusted under 35 U.S.C. 154(b) by 152 days.

(21) Appl. No.: 17/272,096

(22) PCT Filed: Aug. 26, 2019

(86) PCT No.: PCT/CN2019/102632
§ 371 (c)(1),
(2) Date: Feb. 26, 2021

(87) PCT Pub. No.: WO2020/043069
PCT Pub. Date: Mar. 5, 2020

(65) Prior Publication Data

US 2021/0395347 A1 Dec. 23, 2021

(30) Foreign Application Priority Data

Aug. 28, 2018 (CN) ........................ 201810999042.9

(51) Int. Cl.
*C07K 16/10* (2006.01)
*G01N 33/569* (2006.01)

(52) U.S. Cl.
CPC ... *C07K 16/1081* (2013.01); *G01N 33/56983* (2013.01); *C07K 2317/52* (2013.01); *C07K 2317/565* (2013.01); *C07K 2317/567* (2013.01); *C07K 2317/92* (2013.01); *G01N 2333/185* (2013.01); *G01N 2469/10* (2013.01)

(58) Field of Classification Search
CPC ............ C07K 16/1081; C07K 2317/52; C07K 2317/565; C07K 2317/567; C07K 2317/92; C07K 2317/94; C07K 16/10; C07K 2317/56; C07K 2317/20; G01N 33/56983; G01N 2333/185; G01N 2469/10; Y02A 50/30
See application file for complete search history.

(56) References Cited

U.S. PATENT DOCUMENTS

| | | | |
|---|---|---|---|
| 7,371,381 | B2 | 5/2008 | Aaron et al. |
| 2004/0258699 | A1 | 12/2004 | Bowdish et al. |
| 2005/0048070 | A1 | 3/2005 | Ditzel et al. |
| 2013/0164734 | A1 | 6/2013 | Raychaudhuri et al. |
| 2017/0233460 | A1 | 8/2017 | Bosch et al. |

FOREIGN PATENT DOCUMENTS

| | | | |
|---|---|---|---|
| CA | 3111159 | A1 | 3/2020 |
| CA | 3111163 | A1 | 3/2020 |
| CN | 1639185 | A | 7/2005 |
| CN | 103396481 | A | 11/2013 |
| CN | 104357401 | A | 2/2015 |
| CN | 106290847 | A | 1/2017 |
| CN | 109081869 | A | 12/2018 |
| CN | 109134647 | A | 1/2019 |
| TW | 201533059 | A | 9/2015 |
| WO | 2015196192 | A2 | 12/2015 |
| WO | 2017223286 | A1 | 12/2017 |
| WO | 2020043066 | A1 | 3/2020 |

OTHER PUBLICATIONS

Dondelinger M, Filée P, Sauvage E, Quinting B, Muyldermans S, Galleni M, Vandevenne MS. Understanding the Significance and Implications of Antibody Numbering and Antigen-Binding Surface/Residue Definition. Front Immunol. Oct. 16, 2018;9:2278. (Year: 2018).*

Bowie JU, Reidhaar-Olson JF, Lim WA, Sauer RT. Deciphering the message in protein sequences: tolerance to amino acid substitutions. Science. Mar. 16, 1990;247(4948):1306-10. (Year: 1990).*

Winkler K, Kramer A, Küttner G, Seifert M, Scholz C, Wessner H, Schneider-Mergener J, Höhne W. Changing the antigen binding specificity by single point mutations of an anti-p24 (HIV-1) antibody. J Immunol. Oct. 15, 2000;165(8):4505-14. (Year: 2000).*

Kussie PH, Parhami-Seren B, Wysocki LJ, Margolies MN. A single engineered amino acid substitution changes antibody fine specificity. J Immunol. Jan. 1, 1994;152(1):146-52. (Year: 1994).*

Chen Z, Wang J, Bao L, Guo L, Zhang W, Xue Y, Zhou H, Xiao Y, Wang J, Wu F, Deng Y, Qin C, Jin Q. Human monoclonal antibodies targeting the haemagglutinin glycoprotein can neutralize H7N9 influenza virus. Nat Commun. Mar. 30, 2015;6:6714. (Year: 2015).*

Sela-Culang I, Kunik V, Ofran Y. The structural basis of antibody-antigen recognition. Front Immunol. Oct. 8, 2013;4:302. (Year: 2013).*

Sirin S, Apgar JR, Bennett EM, Keating AE. AB-Bind: Antibody binding mutational database for computational affinity predictions. Protein Sci. Feb. 2016;25(2):393-409. Epub Nov. 6, 2015. (Year: 2015).*

Tsuchiya Y, Mizuguchi K. The diversity of H3 loops determines the antigen-binding tendencies of antibody CDR loops. Protein Sci. Apr. 2016;25(4):815-25. Epub Jan. 20, 2016. (Year: 2016).*

(Continued)

*Primary Examiner* — Rachel B Gill
(74) *Attorney, Agent, or Firm* — Kagan Binder, PLLC

(57) ABSTRACT

Provided is an isolated binding protein including an antigen binding domain binding to an NS1 protein, and including specific heavy chain CDR and light chain CDR. The binding protein can specifically identify and bind to NS1, and has relatively high sensitivity and specificity, so as to detect dengue vims. Moreover, the binding protein does not need to be produced by injecting hybridoma cells into mouse peritoneal cavity, while simplifying production, thus stabilizing antibody functionality.

17 Claims, No Drawings

Specification includes a Sequence Listing.

(56) References Cited

OTHER PUBLICATIONS

Collis AV, Brouwer AP, Martin AC. Analysis of the antigen combining site: correlations between length and sequence composition of the hypervariable loops and the nature of the antigen. J Mol Biol. Jan. 10, 2003;325(2):337-54. (Year: 2003).*

Endale A, Medhin G, Darfiro K, Kebede N, Legesse M. Magnitude of Antibody Cross-Reactivity in Medically Important Mosquito-Borne Flaviviruses: A Systematic Review. Infect Drug Resist. Oct. 19, 2021;14:4291-4299. (Year: 2021).*

Fatima, A., (2014) "Development of VHH Antibodies against Dengue Virus Type 2 NS1 and Comparison with Monoclonal Antibodies for Use in Immunological Diagnosis," (Non-official translation) Doctoral Dissertation, p. 1-132, South China University of Technology, Guangzhou, China.

Rocha, L.B., et al. (2017) "Epitope Sequences in Dengue Virus NS1 Protein Identified by Monoclonal Antibodies," Antibodies, 6, 14.

Gelanew, T., and Hunsperger, E. (2018), "Development and characterization of serotype-specific monoclonal antibodies against the dengue virus-4 (DENV-4) non-structural protein (NS1)," Virology Journal, 15:30.

Parameswaran et al., (2013) "Convergent antibody signatures in human dengue," Cell Host Microbe, 13:691-700.

Wong, et al. (2018) "Molecular basis for dengue virus broad cross-neutralization by humanized monoclonal antibody 513," Nature Scientific Reports, 8:8449:1-18.

Gao et al., (2011) "The Preparation and Preliminary Application of the Group-Specific Monoclonal Antibodies Against the Nonstructural Glycoprotein 1 of Dengue Virus," Journal of Tropical Medicine, 11:620-623 and 646.

Shi, et al. (2015) "Clinical Evaluation of the Rapid Detection of Dengue Virus NSI Antigen and IgG/IgM Antibody," Laboratory Medicine, 30:363-366.

Fatima, et al. (2014) "Development of VHH Antibodies against Dengue Virus Type 2 NS1 and Comparison with Monoclonal Antibodies for Use in Immunological Diagnosis," PLOS ONE, 9:1-12.

Puangmanee, et al. (2017) "Characterization of Human Monoclonal Antibodies (Humabs) Specific to Dengue Virus NS1 Protein," JITMM Proceedings, 6:26-34.

Lebani, K., et al., (2017) "Isolation of serotype-specific antibodies against dengue virus non-structural protein 1 using phage display and application in a multiplexed serotyping assay", PLoS ONE, 12(7):1-18.

* cited by examiner

NS1-BINDING PROTEIN

CROSS REFERENCES TO RELATED APPLICATIONS

This application claims priority to International Application No. PCT/CN2019/102632, filed Aug. 26, 2019, which claims priority to Chinese Patent Application No. 201810999042.9, filed on Aug. 28, 2018, and entitled "NS1-Binding Protein", wherein the of said applications are hereby incorporated by reference in their entireties.

REFERENCE TO SEQUENCE LISTING

This application contains a Sequence Listing submitted via USPTO Patent Center. The entire contents of the sequence listing in ASCII text file entitled ACL0096US_Sequence_Listing_3.txt created on Nov. 21, 2023, and having a size of 25,820 bytes, is incorporated herein by reference.

BACKGROUND

Dengue fever (DF) is an acute mosquito-borne infectious disease caused by 4 serotype viruses (DENV-1, DENV-2, DENV-3, and DENV-4) and mainly transmitted by *Aedes aegypti* and *Aedes albopictus*. DF is a harmful arboviral disease with the most widespread distribution and the highest incidence, and is widespread in more than 100 countries and regions in tropical and subtropical Africa, America, Southeast Asia and the Western Pacific region.

Clinically, DF is a serious flu-like disease, and has main manifestations, such as sudden onset, high fever, severe headache, retro-orbital pain, and muscle and joint pain, which may be accompanied by skin rash, lymphadenoma, and leukopenia. DF can affect all people, but its symptoms can vary depending on the age of the patient. This type of disease is generally known as classical dengue fever, spreads rapidly and can cause a large-scale epidemic. The dengue fever, during epidemic, usually has an attack rate among susceptible people in a range from 40% to 50%, which may reach up to a range from 80% to 90%, but very low fatality rate. Dengue hemorrhagic fever, a more serious clinical type, is characterized by high fever, hemorrhage, hepatomegaly, and circulatory failure in severe cases, and has a high fatality rate. DF accompanied by shock syndrome is called dengue shock syndrome.

There is no specific treatment for dengue fever. The fatality rate of dengue hemorrhagic fever can exceed 20% without proper treatment, but can be less than 1% with effective treatment. Key points for the diagnosis of dengue fever are shown as follows: 1) epidemiological data: activities in the 15 days before the onset of dengue fever, such as whether the patient has been to the endemic area and got mosquito bites; 2) clinical characteristics: sudden onset, fever, "three kinds of pain and three kinds of rubeosis", and rash; 3) laboratory examination: decreased white blood cells and platelets, positive serum-specific IgM, 4 times higher IgG in the recovery phase than that in the acute phase, isolated virus or specific antigen. Clinically used methods for dengue virus detection include virus culture, serological test, viral nucleic acid detection, etc. Virus isolation takes a long time, which makes it impossible to achieve rapid diagnosis, and conventional serological diagnosis is interfered due to the existence of extensive cross-reactions. The colloidal gold-labeled immunochromatographic method is fast and simple, requires no special equipment, and enables on-site detection and it has become a research focus in the rapid diagnosis of infectious diseases. NS1 protein is the only glycoprotein among the non-structural proteins of dengue virus. This NS1 protein has extremely strong antigenicity and does not trigger antibody-dependent enhancement (ADE) of infection, thus it can be used as a target for immunoassay. Such immunoassay requires a specific monoclonal antibody against the NS1 protein. Conventionally, mouse-derived monoclonal antibodies are used in clinical practice. Mouse monoclonal antibodies have been widely used in scientific research, clinical diagnosis and treatment for a long time. However, the hybridoma method is greatly affected by individual mice due to the requirement of production in abdominal cavity of the mice, which leads to unstable production and large batch-to-batch differences, and is difficult to purify due to the existence of mouse autoantibodies.

SUMMARY

In the present disclosure, based on an anti-dengue virus NS1 7D9 monoclonal antibody newly obtained by screening, sequences of CDR regions of the antibody are identified through cloning, identification and gene structure analysis, a corresponding isolated binding protein comprising an antigen-binding domain that binds to NS1 protein is constructed, a corresponding eukaryotic cell expression system is established for producing and purifying the binding protein.

The present disclosure provides an isolated binding protein comprising an antigen-binding domain that binds to NS1 protein, wherein the antigen-binding domain comprises at least one complementarity determining region, which has an amino acid sequence as follows, or which has at least 80% sequence identity to the complementarity determining region having the amino acid sequence as follows and has an affinity for the NS1 protein at a KD value that is less than or equal to $6.12\times10^{-8}$ mol/L:

a complementarity determining region CDR1-VH having a sequence of A-S-G-Y-X1-F-T-G-X2-Y-M-H (SEQ ID NO: 23), where X1 is S or T, and X2 is F, Y or L;

a complementarity determining region CDR2-VH having a sequence of R-V-N-P-X1-N-G-G-X2-S-Y-N-Q-K-F-X3-G (SEQ ID NO: 24), where X1 is Q, D or N, X2 is S or T, and X3 is V, I or F;

a complementarity determining region CDR3-VH having a sequence of A-X1-E-G-X 2-H-Y-D-R-A (SEQ ID NO: 25), where X1 is Q, N or R, and X2 is V, F or Y;

a complementarity determining region CDR1-VL having a sequence of Q-S-L-L-Y-X 1-S-N-X2-K-N-S-L-A (SEQ ID NO: 26), where X1 is S or T, and X2 is N, Q or H;

a complementarity determining region CDR2-VL having a sequence of W-A-S-T-X1-E-S (SEQ ID NO: 27), where X1 is Q, R or N;

a complementarity determining region CDR3-VL having a sequence of Q-Q-Y-X1-T-Y-X2-Y-T (SEQ ID NO: 28), where X1 is F, Y or V, and X2 is A, P or G.

For example, in the complementarity determining region CDR1-VH, X1 is S (SEQ ID NO: 29);

in the complementarity determining region CDR2-VH, X2 is T, and X3 is I (SEQ ID NO: 30);

in the complementarity determining region CDR1-VL, X2 is Q (SEQ ID NO: 31);

in the complementarity determining region CDR3-VL, X2 is P (SEQ ID NO: 32).

For example, in the complementarity determining region CDR1-VH, X2 is F (SEQ ID NO: 33).

For example, in the complementarity determining region CDR1-VH, X2 is Y (SEQ ID NO: 34).

For example, in the complementarity determining region CDR1-VH, X2 is L (SEQ ID NO: 35).

For example, in the complementarity determining region CDR2-VH, X1 is Q (SEQ ID NO: 36).

For example, in the complementarity determining region CDR2-VH, X1 is D (SEQ ID NO: 37).

For example, in the complementarity determining region CDR2-VH, X1 is N (SEQ ID NO: 38).

For example, in the complementarity determining region CDR3-VH, X1 is Q, and X2 is V (SEQ ID NO: 39).

For example, in the complementarity determining region CDR3-VH, X1 is Q, and X2 is F (SEQ ID NO: 40).

For example, in the complementarity determining region CDR3-VH, X1 is Q, and X2 is Y (SEQ ID NO: 41).

For example, in the complementarity determining region CDR3-VH, X1 is N, and X2 is V (SEQ ID NO: 42).

For example, in the complementarity determining region CDR3-VH, X1 is N, and X2 is F (SEQ ID NO: 43).

For example, in the complementarity determining region CDR3-VH, X1 is N, and X2 is Y (SEQ ID NO: 44).

For example, in the complementarity determining region CDR3-VH, X1 is R, and X2 is V (SEQ ID NO: 45).

For example, in the complementarity determining region CDR3-VH, X1 is R, and X2 is F (SEQ ID NO: 46).

For example, in the complementarity determining region CDR3-VH, X1 is R, and X2 is Y (SEQ ID NO: 47).

For example, in the complementarity determining region CDR1-VL, X1 is S (SEQ ID NO: 48).

For example, in the complementarity determining region CDR1-VL, X1 is T (SEQ ID NO: 49).

For example, in the complementarity determining region CDR2-VL, X1 is Q (SEQ ID NO: 50).

For example, in the complementarity determining region CDR2-VL, X1 is R (SEQ ID NO: 51).

For example, in the complementarity determining region CDR2-VL, X1 is N (SEQ ID NO: 52).

For example, in the complementarity determining region CDR3-VL, X1 is F (SEQ ID NO: 53).

For example, in the complementarity determining region CDR3-VL, X1 is Y (SEQ ID NO: 54).

For example, in the complementarity determining region CDR3-VL, X1 is V (SEQ ID NO: 55).

In one or more embodiments, the amino acids at the corresponding sites of the complementarity determining regions are as follows:

| Site | CDR-VH1 X2 | CDR-VH2 X1 | CDR-VH3 X1/X2 | CDR-VL1 X1 | CDR-VL2 X1 | CDR-VL3 X1 |
|---|---|---|---|---|---|---|
| Mutation 1 | F | Q | Q/V | S | Q | F |
| Mutation 1-1 | Y | D | Q/F | T | R | Y |
| Mutation 1-2 | L | N | Q/Y | S | N | V |
| Mutation 1-3 | F | Q | N/V | T | Q | F |
| Mutation 1-4 | Y | D | N/F | S | R | Y |
| Mutation 1-5 | L | N | N/Y | T | N | V |
| Mutation 1-6 | F | Q | R/V | S | Q | F |

-continued

| Site | CDR-VH1 X2 | CDR-VH2 X1 | CDR-VH3 X1/X2 | CDR-VL1 X1 | CDR-VL2 X1 | CDR-VL3 X1 |
|---|---|---|---|---|---|---|
| Mutation 1-7 | Y | D | R/F | T | R | Y |
| Mutation 1-8 | L | N | R/Y | S | N | V |
| Mutation 1-9 | F | D | Q/V | T | Q | F |
| Mutation 1-10 | Y | N | Q/F | S | R | Y |
| Mutation 1-11 | L | Q | Q/Y | T | N | V |
| Mutation 1-12 | F | D | N/V | S | Q | F |
| Mutation 1-13 | Y | N | N/F | T | R | Y |
| Mutation 1-14 | L | Q | N/Y | S | N | V |
| Mutation 1-15 | F | D | R/V | T | Q | F |
| Mutation 1-16 | Y | N | R/F | S | R | Y |
| Mutation 1-17 | L | Q | R/Y | T | N | V |
| Mutation 1-18 | F | D | Q/F | S | R | F |
| Mutation 1-19 | Y | N | Q/Y | T | N | Y |
| Mutation 1-20 | L | Q | N/V | S | Q | V |
| Mutation 1-21 | F | Q | N/F | T | R | F |
| Mutation 1-22 | Y | D | Q/F | S | N | Y |
| Mutation 1-23 | L | N | Q/Y | T | Q | V |
| Mutation 1-24 | F | Q | N/V | S | N | F |
| Mutation 1-25 | Y | Q | N/F | T | Q | F |
| Mutation 1-26 | L | D | Q/Y | S | R | Y |
| Mutation 1-27 | F | N | N/V | T | N | V |
| Mutation 1-28 | Y | Q | N/F | S | N | F |
| Mutation 1-29 | L | D | N/Y | T | Q | Y |
| Mutation 1-30 | F | N | Q/Y | S | R | V |
| Mutation 1-31 | Y | Q | N/V | T | N | V |
| Mutation 1-32 | L | D | N/F | S | Q | F |
| Mutation 1-33 | F | D | N/Y | T | R | Y |
| Mutation 1-34 | Y | N | N/V | S | N | V |
| Mutation 1-35 | L | Q | N/F | T | Q | F |
| Mutation 1-36 | F | D | N/Y | S | Q | Y |
| Mutation 1-37 | Y | N | R/V | T | R | V |
| Mutation 1-38 | L | Q | N/F | S | N | F |
| Mutation 1-39 | F | D | N/Y | S | Q | F |
| Mutation 1-40 | Y | N | R/V | S | R | V |

For example, the binding protein comprises at least 3 CDRs; or the binding protein comprises at least 6 CDRs.

For example, the binding protein is one of nanobody, $F(ab')_2$, Fab', Fab, Fv, scFv, bispecific antibody, and antibody minimal recognition unit.

For example, the binding protein comprises light chain framework regions VL-FR1, VL-FR2, VL-FR3 and VL-FR4 having sequences as set forth in SEQ ID NO: 1 to 4, respectively, and/or heavy chain framework regions VH-FR1, VH-FR2, VH-FR3 and VH-FR4 having sequences as set forth in SEQ ID NO: 5 to 8, respectively.

In one or more embodiments, the binding protein further comprises a constant region sequence of an antibody.

For example, the constant region sequence is a sequence of a constant region of any one selected from the group consisting of IgG1, IgG2, IgG3, IgG4, IgA, IgM, IgE, and IgD.

The constant region is derived from the following species: cattle, horse, dairy cow, pig, sheep, goat, rat, mouse, dog, cat, rabbit, camel, donkey, deer, mink, chicken, duck, goose, turkey, gamecock, or human.

For example, the constant region is derived from mouse.

The constant region sequence of a light chain is as set forth in SEQ ID NO: 9.

The constant region sequence of a heavy chain is as set forth in SEQ ID NO: 10.

The present disclosure further provides a nucleic acid encoding the binding protein as described above.

The present disclosure further provides a vector comprising the nucleic acid as described above.

The present disclosure further provides a host cell comprising the nucleic acid as described above or the vector as described above.

The present disclosure further provides a kit comprising one or more of the binding proteins, the nucleic acid or the vector as described above.

In one or more embodiments, the kit further comprises a label for labeling the binding protein.

The present disclosure further provides a method for producing the binding protein as described above comprising a step of preparing the nucleic acid or the vector as described above.

Optionally, the method comprises the following steps:

culturing the host cells as described above in a culture medium, and recovering binding proteins thus produced from the culture medium or from the cultured host cells.

In addition, the present disclosure further provides use of the binding protein as described above in preparation of a product for detecting dengue fever infection.

The isolated binding protein comprising an antigen-binding domain that binds to NS1 protein provided in the present disclosure includes specific heavy chain CDRs and light chain CDRs. The binding protein can specifically recognize and bind to the NS1 protein and has high sensitivity and specificity, thereby enabling detection of dengue fever virus. Moreover, the binding protein may be produced without the mouse abdominal cavity for inducing hybridoma cells, making less difficulty in production and more stable antibody function.

DETAILED DESCRIPTION OF THE EMBODIMENTS

Unless otherwise defined herein, scientific and technical terms used in connection with the present disclosure shall have the meanings that are commonly understood by those of ordinary skill in the art. The meaning and scope of the terms should be clear, however, in the event of any latent ambiguity, definitions provided herein take precedent over any dictionary or extrinsic definition. In the present disclosure, the use of "or" means "and/or" unless stated otherwise. Furthermore, the use of the term "include/comprise", as well as other forms, is not limiting.

Generally, nomenclatures used in connection with, and techniques of, cell and tissue culture, molecular biology, immunology, microbiology, genetics, and protein and nucleic acid chemistry and hybridization described herein are those well-known and commonly used in the art. The methods and techniques of the present disclosure are generally performed according to conventional methods well known in the art and as described in various general and more specific references that are cited and discussed throughout the present specification, unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art.

In order that the present disclosure may be more readily understood, select terms are defined below.

The term "amino acid" refers to naturally occurring or non-naturally occurring carboxy a-amino acids. The term "amino acid" as used in the present disclosure may include naturally occurring amino acids and non-naturally occurring amino acids. The naturally occurring amino acids include: alanine (three-letter code: Ala, single-letter code: A), arginine (Arg, R), asparagine (Asn, N), aspartic acid (Asp, D), cysteine (Cys, C), glutamine (Gln, Q), glutamic acid (Glu, E), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and Valine (Val, V). The non-naturally occurring amino acids include but are not limited to a-aminoadipate, aminobutyric acid, citrulline, homocitrulline, homoleucine, homoarginine, hydroxyproline, norleucine, pyridylalanine, sarcosine, and the like.

The term "isolated binding protein" is a protein which by virtue of its origin or source of derivation is not associated with naturally associated components that accompany it in its native state; which is substantially free of other proteins from the same species; which is expressed by a cell from a different species; or which does not found in nature. Thus, a polypeptide that is chemically synthesized or synthesized in a cellular system different from the cell from which it naturally originates will be "isolated" from its naturally associated components. A protein may also be rendered substantially free of naturally associated components by isolation, for example, using protein purification techniques well known in the art.

The term "isolated binding protein comprising an antigen-binding domain" refers to all proteins/protein fragments containing CDR regions. The term "antibody" includes polyclonal antibodies, monoclonal antibodies, and antigen-compound-binding fragments of these antibodies, including Fab, F(ab')2, Fd, Fv, scFv, bispecific antibody, and antibody minimal recognition unit, as well as single chain derivatives of these antibodies and fragments. The type of the antibody can be selected from the group consisting of IgG1, IgG2, IgG3, IgG4, IgA, IgM, IgE, and IgD. Moreover, the term "antibody" includes naturally-occurring antibodies, as well as non-naturally-occurring antibodies including, for example, chimeric, bifunctional and humanized antibodies, and relevant synthetic isoforms. The term "antibody" can be used interchangeably with "immunoglobulin".

A "variable region" or "variable domain" of an antibody refers to the amino terminal domain of a heavy or light chain of the antibody. The variable domain of the heavy chain is referred to as "VH". The variable domain of the light chain is referred to as "VL". These domains are usually the most variable parts of antibodies and contain an antigen binding site. The variable region of light or heavy chain is composed of three hypervariable regions termed "complementarity determining regions" or "CDRs", and framework regions that separates the three CDRs. The framework regions of the antibody functions to locate the CDRs and bring the CDRs into alignment, and the CDRs are mainly responsible for binding to the antigen.

As used herein, the term "bispecific antibody" or "bifunctional antibody" refers to an artificial hybrid binding protein with two different pairs of heavy/light chains and two different binding sites. Bispecific binding proteins can be produced by a variety of methods, including hybridoma fusion or Fab' fragments linking.

As used herein, the term "sequence identity" refers to the similarity between at least two different sequences. This percent identity can be determined by standard algorithms, for example, the Basic Local Alignment Search Tool (BLAST); the algorithm established by Needleman et al.; or the algorithm established by Meyers et al. In one or more embodiments, a set of parameters may be the Blosum 62 scoring matrix with a gap penalty of 12, a gap extend penalty of 4, and a frameshift gap penalty of 5. In one or more embodiments, the percent identity between two amino acid or nucleotide sequences can also be determined using the algorithm as described in Meyers and Miller ((1989) CABIOS 4:11-17), which has been incorporated into the ALIGN program (version 2.0), using a PAM120 weight residue table, a gap length penalty of 12, and a gap penalty of 4. The percent identity is usually calculated by comparing sequences of similar length.

As used herein, the term "affinity" refers to the binding strength of the antigen-binding domain of a binding protein or antibody to an antigen or epitope. Affinity can be measured by KD value. A smaller KD value means a greater affinity.

The present disclosure provides an isolated binding protein comprising an antigen-binding domain that binds to NS1 protein, wherein the antigen-binding domain comprises at least one complementarity determining region, which has an amino acid sequence as follows, or which has at least 80% sequence identity to the complementarity determining region having the amino acid sequence as follows and has an affinity for the NS1 protein at a KD value that is less than or equal to $6.12\times10^{-8}$ mol/L:

a complementarity determining region CDR1-VH having a sequence of A-S-G-Y-X1-F-T-G-X2-Y-M-H (SEQ ID NO: 23), where X1 is S or T, and X2 is F, Y or L;

a complementarity determining region CDR2-VH having a sequence of R-V-N-P-X1-N-G-G-X2-S-Y-N-Q-K-F-X3-G (SEQ ID NO: 24), where X1 is Q, D or N, X2 is S or T, and X3 is V, I or F;

a complementarity determining region CDR3-VH having a sequence of A-X1-E-G-X 2-H-Y-D-R-A (SEQ ID NO: 25), where X1 is Q, N or R, and X2 is V, F or Y;

a complementarity determining region CDR1-VL having a sequence of Q-S-L-L-Y-X 1-S-N-X2-K-N-S-L-A (SEQ ID NO: 26), where X1 is S or T, and X2 is N, Q or H;

a complementarity determining region CDR2-VL having a sequence of W-A-S-T-X1-E-S (SEQ ID NO: 27), where X1 is Q, R or N;

a complementarity determining region CDR3-VL having a sequence of Q-Q-Y-X1-T-Y-X2-Y-T (SEQ ID NO: 28), where X1 is F, Y or V, and X2 is A, P or G.

In one or more embodiments, X1 appearing in the six CDR regions of the binding protein described in the present disclosure each independently represents an amino acid defined in the present disclosure; X2 appearing in the six CDR regions of the binding protein described in the present disclosure each independently represents an amino acid defined in the present disclosure; and X3 appearing in the six CDR regions of the binding protein described in the present disclosure each independently represents an amino acid defined in the present disclosure.

It is well known in the art that the binding specificity and affinity of antibodies are mainly determined by CDR sequences. According to mature and well-known existing technologies, the amino acid sequences of non-CDR regions can be easily modified to obtain variants with similar biological activity. Therefore, the present disclosure also includes "functional derivatives" of the binding protein. The "functional derivatives" refers to variants with amino acid substitution. A functional derivative retains detectable protein binding activity, preferably the activity of an antibody that can bind to the NS1 protein. The "functional derivatives" may comprise "variants" and "fragments". They have exactly the same CDR sequences as the binding proteins described in the present disclosure, thus have similar biological activities.

In some embodiments, the antigen-binding domain has at least 50%, or at least 55%, or at least 60%, or at least 65%, or at least 70%, or at least 75%, or at least 80%, or at least 85%, or at least 90%, or at least 91%, or at least 92%, or at least 93%, or at least 94%, or at least 95%, or at least 96%, or at least 97%, or at least 98%, or at least 99% sequence identity to the complementarity determining region having the amino acid sequence as follows and has an affinity for the NS1 protein at a KD value that is less than or equal to $6.12\times10^{-8}$ mol/L, for example, equal to $3.13\times10^{-10}$ mol/L, $4.45\times10^{-10}$ mol/L, $5.34\times10^{-10}$ mol/L, $7.05\times10^{-10}$ mol/L, $2.32\times10^{-9}$ mol/L, $2.94\times10^{-9}$ mol/L, $3.10\times10^{-9}$ mol/L, $3.54\times10^{-9}$ mol/L, $3.90\times10^{-9}$ mol/L, or $6.12\times10^{-8}$ mol/L, or greater than or equal to $3.13\times10^{-10}$ mol/L and less than or equal to $6.12\times10^{-8}$ mol/L.

In one or more embodiments, in the complementarity determining region CDR1-VH, X1 is S (SEQ ID NO: 29);

in the complementarity determining region CDR2-VH, X2 is T, and X3 is I (SEQ ID NO: 30);

in the complementarity determining region CDR1-VL, X2 is Q (SEQ ID NO: 31);

in the complementarity determining region CDR3-VL, X2 is P (SEQ ID NO: 32).

In one or more embodiments, in the complementarity determining region CDR1-VH, X2 is F (SEQ ID NO: 33).

In one or more embodiments, in the complementarity determining region CDR1-VH, X2 is Y (SEQ ID NO: 34).

In one or more embodiments, in the complementarity determining region CDR1-VH, X2 is L (SEQ ID NO: 35).

In one or more embodiments, in the complementarity determining region CDR2-VH, X1 is D (SEQ ID NO: 37).

In one or more embodiments, in the complementarity determining region CDR2-VH, X1 is N (SEQ ID NO: 38).

In one or more embodiments, in the complementarity determining region CDR3-VH, X1 is Q, and X2 is V (SEQ ID NO: 39).

In one or more embodiments, in the complementarity determining region CDR3-VH, X1 is Q, and X2 is F (SEQ ID NO: 40).

In one or more embodiments, in the complementarity determining region CDR3-VH, X1 is Q, and X2 is Y (SEQ ID NO: 41).

In one or more embodiments, in the complementarity determining region CDR3-VH, X1 is N, and X2 is V (SEQ ID NO: 42).

In one or more embodiments, in the complementarity determining region CDR3-VH, X1 is N, and X2 is F (SEQ ID NO: 43).

In one or more embodiments, in the complementarity determining region CDR3-VH, X1 is N, and X2 is Y (SEQ ID NO: 44).

In one or more embodiments, in the complementarity determining region CDR3-VH, X1 is R, and X2 is V (SEQ ID NO: 45).

In one or more embodiments, in the complementarity determining region CDR3-VH, X1 is R, and X2 is F (SEQ ID NO: 46).

In one or more embodiments, in the complementarity determining region CDR3-VH, X1 is R, and X2 is Y (SEQ ID NO: 47).

In one or more embodiments, in the complementarity determining region CDR1-VL, X1 is S (SEQ ID NO: 48).

In one or more embodiments, in the complementarity determining region CDR1-VL, X1 is T (SEQ ID NO: 49).

In one or more embodiments, in the complementarity determining region CDR2-VL, X1 is Q (SEQ ID NO: 50).

In one or more embodiments, in the complementarity determining region CDR2-VL, X1 is R (SEQ ID NO: 51).

In one or more embodiments, in the complementarity determining region CDR2-VL, X1 is N (SEQ ID NO: 52).

In one or more embodiments, in the complementarity determining region CDR3-VL, X1 is F (SEQ ID NO: 53).

In one or more embodiments, in the complementarity determining region CDR3-VL, X1 is Y (SEQ ID NO: 54).

In one or more embodiments, in the complementarity determining region CDR3-VL, X1 is V (SEQ ID NO: 55).

In one or more embodiments, the binding protein includes at least 3 CDRs; or the binding protein includes at least 6 CDRs.

In one or more embodiments, the binding protein is an intact antibody comprising a variable region and a constant region.

In one or more embodiments, the binding protein is one of nanobody, $F(ab')_2$, Fab', Fab, Fv, scFv, bispecific antibody, and antibody minimal recognition unit.

In one or more embodiments, the binding protein comprises light chain framework regions VL-FR1, VL-FR2, VL-FR3 and VL-FR4 having sequences as set forth in SEQ ID NO: 1 to 4, respectively, and/or heavy chain framework regions VH-FR1, VH-FR2, VH-FR3 and VH-FR4 having sequences as set forth in SEQ ID NO: 5 to 8, respectively.

In one or more embodiments, the binding protein further comprises a constant region sequence of an antibody.

In one or more embodiments, the constant region sequence is a sequence of a constant region of any one selected from the group consisting of IgG1, IgG2, IgG3, IgG4, IgA, IgM, IgE, and IgD.

In one or more embodiments, the constant region is derived from the following species: cattle, horse, dairy cow, pig, sheep, goat, rat, mouse, dog, cat, rabbit, camel, donkey, deer, mink, chicken, duck, goose, turkey, gamecock, or human.

In one or more embodiments, the constant region is derived from mouse.

The constant region sequence of a light chain is as set forth in SEQ ID NO: 9.

The constant region sequence of a heavy chain is as set forth in SEQ ID NO: 10.

In one or more embodiments, the present disclosure provides a nucleic acid sequence encoding the binding protein. The nucleic acid sequence herein provides conservatively substituted variants (for example, degenerate codon-substituted) and complementary sequences thereof. The terms "nucleic acid" and "polynucleotide" are synonymous, and include genes, cDNA molecules, mRNA molecules and their fragments such as oligonucleotides.

In one or more embodiments, the present disclosure provides an expression vector containing the nucleic acid sequence encoding the binding protein, wherein the nucleic acid sequence is operably linked to at least one regulatory sequence. "Operably linked" means that a coding sequence is linked to a regulatory sequence in a manner that allows the expression of the coding sequence. The regulatory sequence is selected to direct the expression of the interest protein in a suitable host cell, and include a promoter, an enhancer and other expression control elements.

The vector herein may refer to a molecule or agent that contains the nucleic acid of the present disclosure or a fragment thereof, can carry genetic information, and can deliver the genetic information to cells. Typical vectors include plasmids, viruses, bacteriophages, cosmids and minichromosomes. The vector can be a cloning vector (that is, a vector for transferring genetic information into a cell, which can be propagated and selected for the presence of the genetic information) or an expression vector (that is, a vector that contains the necessary genetic elements to allow the expression of genetic information in the vector to be expressed in a cell). Therefore, the cloning vector may contain a selective marker and an origin of replication that matches the cell type specified by the cloning vector, and the expression vector contains regulatory elements necessary for affecting expression in the specified target cell.

The nucleic acid of the present disclosure or a fragment thereof can be inserted into a suitable vector to form the cloning vector or expression vector carrying the nucleic acid fragment of the present disclosure. This new vector is also part of this disclosure. The vector can include plasmids, phages, cosmids, minichromosomes or viruses, as well as naked DNA that is only transiently expressed in specific cells. The cloning vector and the expression vector of the present disclosure can replicate spontaneously, and therefore can provide a high copy number for the purpose of high-level expression or high-level replication for subsequent cloning. The expression vector may include a promoter for driving the expression of the nucleic acid fragment of the present disclosure, optionally a nucleic acid sequence encoding a signal peptide that enables the peptide expression product to be secreted or to be integrated into the membrane, the nucleic acid fragment of the present disclosure, and optionally a nucleic acid sequence encoding a terminator. In the case where the expression vector is manipulated in the production strain or cell line, the vector may be or may not be integrated into the genome of the host cell when introduced into the host cell. The vector usually carries a replication site and a marker sequence that can provide phenotypic selection in transformed cells.

The expression vector of the present disclosure is used to transform host cells. Such a transformed cell is also part of the present disclosure, and may be cultured cells or cell lines used to propagate the nucleic acid fragment and vector of the present disclosure, or to recombinantly prepare the polypeptide of the present disclosure. The transformed cell of the present disclosure includes microorganisms such as bacteria, for example, *Escherichia coli*, *Bacillus*, etc. The host cells further include cells from multicellular organisms such as fungi, insect cells, plant cells or mammalian cells, preferably cells from mammals, such as CHO cells. The transformed cell is capable of replicating the nucleic acid fragment of the present disclosure. When the peptide combination of the present disclosure is recombinantly prepared, the expression product can be exported to a culture medium or carried on the surface of the transformed cell.

In one or more embodiments, the binding protein provided in the present disclosure can be used for detection of the presence of one or more target molecules in a biological sample. The term "detection", when used herein, includes quantitative or qualitative detection. In one or more embodiments, the biological sample comprises cells or tissues.

As used herein, the term "colloidal gold immunoassay" is an immunolabeling technique in which colloidal gold is used as a tracing marker for antigen and/or antibody. Colloidal gold is formed by polymerizing chloroauric acid under the action of reducing agents such as white phosphorus, ascorbic acid, sodium citrate, tannic acid and the like into gold particles of a specific size, which become a stable colloidal state due to static electricity.

The immunoassay of the present disclosure includes colloidal gold immunoassay, as well as ELISA, chemiluminescence, and other tests or methods that utilize antigen-antibody reactions.

In one or more embodiments, the present disclosure provides an article (eg, a kit) that contains materials that can be used for the diagnosis of dengue virus infection. The article includes a container and a label or package instruction on or along with the container. The suitable container includes, for example, bottles or syringes. The container can be made of various materials such as glass or plastic. The container contains a composition, alone or in combination with another composition that is effective for diagnosing dengue fever. At least one active reagent in the composition is the binding protein provided in the present disclosure.

In one or more embodiments, a detection kit containing the binding protein, the nucleic acid, or the vector described herein, is provided herein.

A method for detecting an NS1 protein antigen in a test sample comprises:

A) contacting the NS1 protein antigen in the test sample with the binding protein as described above under a condition sufficient for the occurrence of antibody/antigen binding reaction, to form an immune complex; and B) detecting the presence of the immune complex, the presence of the complex indicating the presence of the NS1 protein antigen in the test sample;

In one or more embodiments, the binding protein can be labeled with an indicator for showing signal intensity, so that the complex is easily detected.

In one or more embodiments, in step A), the immune complex further comprises a second antibody that binds to the binding protein.

In one or more embodiments, the binding protein, in a form of a first antibody, forms a paired antibody with the second antibody, for binding to different epitopes of the NS1 protein.

The second antibody can be labeled with an indicator for showing signal intensity, so that the complex is easily detected.

In one or more embodiments, in step A), the immune complex further comprises a second antibody that binds to the NS1 protein antigen.

In one or more embodiments, the binding protein serves as the antigen of the second antibody. The second antibody can be labeled with an indicator for showing signal intensity, so that the complex is easily detected.

In one or more embodiments, the indicator for showing signal intensity includes any of fluorescent substance, quantum dot, digoxigenin-labeled probe, biotin, radioisotope, radiocontrast agent, paramagnetic ion fluorescent microsphere, electron-dense material, chemiluminescent markers, ultrasound contrast agents, photosensitizers, colloidal gold or enzymes.

In one or more embodiments, the fluorescent substance includes any of Alexa 350, Alexa 405, Alexa 430, Alexa 488, Alexa 555, Alexa 647, AMCA, aminoacridine, BODIPY 630/650, BODIPY 650/665, BODIPY-FL, BODIPY-R6G, BODIPY-TMR, BODIPY-TRX, 5-carboxy-4',5'-dichloro-2',7'-dimethoxyfluorescein, 5-carboxy-2',4',5',7'-tetrachlorofluorescein, 5-carboxyfluorescein, 5-carboxyrhodamine, 6-carboxyrhodamine, 6-carboxytetramethylrhodamine, Cascade Blue, Cy2, Cy3, Cy5, Cy7, 6-FAM, dansyl chloride, fluorescein, HEX, 6-JOE, NBD (7-nitrobenzo-2-oxa-1,3-diazole), Oregon Green 488, Oregon Green 500, Oregon Green 514, Pacific Blue, o-phthalic acid, p-phthalic acid, m-phthalic acid, cresol solid violet, cresol blue violet, brilliant cresol blue, p-aminobenzoic acid, erythrosine, phthalocyanine, azomethine, cyanine, xanthine, succinylfluorescein, rare earth metal cryptate, europium tris-bipyridine diamine, europium cryptate or chelate, diamine, biscyanin, La Jolla blue dye, allophycocyanin, B-allococyanin, C-phycocyanin, R-phycocyanin, thiamine, phycoerythrin, R-phycoerythrin, REG, rhodamine green, rhodamine isothiocyanate, rhodamine red, ROX, TAMRA, TET, TRIT (tetramethylrhodamine isothiol), tetramethylrhodamine and Texas Red.

In one or more embodiments, the radioisotope includes any of $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94}$mTc, $^{94}$Tc, $^{99}$mTc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52}$mMn, $^{55}$Co, $^{72}$As, $^{75}$Br, $^{76}$Br, $^{82}$mRb and $^{83}$Sr.

In one or more embodiments, the enzymes include any of horseradish peroxidase, alkaline phosphatase and glucose oxidase.

In one or more embodiments, the fluorescent microsphere is a polystyrene fluorescent microsphere, inside which fluorescent europium, a rare earth ion, is packaged.

In one or more embodiments, the present disclosure provides a kit for determining the presence of the NS1 protein in, for example, a subject infected with dengue fever. The kit includes at least one binding protein provided in the present disclosure, a related buffer, and a reagent required for reacting a liquid sample with the binding protein, and a reagent for determining the presence of a positive or negative binding reaction between the NS1 protein and the binding protein. In order to determine the presence of the NS1 protein, for example, a binding protein with a label can be used as an antibody in the kit, wherein the label can be any suitable label, such as a colloidal gold label.

The present disclosure further provides the use of the binding protein as described herein in detection of dengue fever infection.

The present disclosure further provides a method for detecting dengue fever infection, including:

A) contacting a sample from a subject with the binding protein as described above for a binding reaction under a condition sufficient for the occurrence of the binding reaction, B) detecting an immune complex produced by the binding reaction, wherein the presence of the immune complex indicates the presence of the dengue fever infection.

In one or more embodiments, the method is based on fluorescence immunoassay, chemiluminescence immunoassay, immunochromatography, radioimmunoassay and/or enzyme-linked immunoassay.

In one or more embodiments, the method is based on enzyme-linked immunoassay.

In one or more embodiments, the method is based on colloidal gold immunoassay.

In one or more embodiments, the sample is selected from at least one of whole blood, peripheral blood, serum or plasma.

In one or more embodiments, the subject is a mammal, such as a primate, for example, human.

A number of examples are provided below to illustrate the present disclosure, rather than limiting the scope of the present disclosure.

Example 1

In this example, the restriction endonuclease and Prime Star DNA Polymerase were purchased from Takara. MagExtractor-RNA Extraction kit was purchased from TOYOBO. SMARTER™ RACE cDNA Amplification kit was purchased from Takara. pMD-18T vector was purchased from Takara. Plasmid Extraction kit was purchased from Tiangen. The primer synthesis and gene sequencing were done by Invitrogen. The hybridoma cell line stain that secretes the anti-dengue virus NS1 7D9 monoclonal antibody was that newly obtained by screening by the applicant.

1.1. Primers

```
5'RACE primers for amplifying a heavy chain and a
light chain SMARTER II A Oligonucleotide:
                                        (SEQ ID NO: 13)
5'-AAGCAGTGGTATCAACGCAGAGTACXXXXX-3';

5'-RACE CDS Primer (5'-CDS):
                                        (SEQ ID NO: 14)
5'-(T)25VN-3'(N=A, C, G, or T; V=A, G, or C),;

Universal Primer A Mix (UPM)
                                        (SEQ ID NO: 15)
5'-CTAATACGACTCACTATAGGGCAAGCAGTGGTATCAACGCAGAGT-
3';

Nested-Universal Primer A (NUP):
                                        (SEQ ID NO: 16)
5'-AAGCAGTGGTATCAACGCAGAGT-3';

mkR:
                                        (SEQ ID NO: 17)
5'-TTTTCCTTTTGAATTCCTAACACTCATTCCTGTTGAAGC-3';

mHR:
                                        (SEQ ID NO: 18)
5'-ACACTCATTCCTGTTGAAGCTCTTGACAATG-3'.
```

1.2. Gene Cloning and Sequencing of Antibody Variable Regions

RNA was extracted from the hybridoma cell line that secretes the anti-dengue virus NS1 7D9 monoclonal antibody, and used to synthesize a first-strand cDNA by utilizing the SMARTER™ RACE cDNA Amplification kit and the SMARTER II A Oligonucleotide and 5'-CDS primer in the kit. The obtained product, i.e. the first-strand cDNA, was served as a template for PCR amplification. A light chain gene was amplified with the Universal Primer A Mix (UPM), the Nested-Universal Primer A (NUP) and the mkR primer, and a heavy chain gene was amplified with the Universal Primer A Mix (UPM), the Nested-Universal Primer A (NUP) and the mHR primer. A target band in size of about 0.8 KB was amplified with the primer pair for light chain, while a target band in size of about 1.4 KB was amplified with the primer pair for heavy chain. After purification by agarose gel electrophoresis and recovery, the product was subjected to poly-A tail addition reaction and inserted into the pMD-18T vector prior to transformation into DH5a competent cells. After colonies grew visibly, for each of the heavy chain gene and light chain gene, 4 clones were picked, and then sent to Invitrogen for sequencing.

1.3. Sequence Analysis of Variable Region Genes of Anti-Dengue Virus NS1 7D9 Antibody The gene sequences obtained by the above sequencing were put in the IMGT antibody database and analyzed using VNTI11.5 software, confirming that the genes amplified with the primer pairs for heavy chain and light chain were correct. In the gene fragment amplified with the primer pair for light chain, the VL gene, belonging to the VkII gene family, has a 339 bp sequence with a 57 bp leader peptide sequence upstream; and in the gene fragment amplified with the primer pair for heavy chain, the VL gene, belonging to the VH1 gene family, has a 364 bp sequence with a 57 bp leader peptide sequence upstream.

1.4. Construction of Recombinant Antibody Expression Plasmid pcDNA™ 3.4 TOPO® vector is a constructed recombinant antibody eukaryotic expression vector. Multiple cloning sites, such as HindIII, BamHI, EcoRI, and the like, were introduced into the vector, which was named pcDNA 3.4A expression vector (hereafter referred to as 3.4A expression vector for short). According to the sequencing results of the above-mentioned antibody genes in pMD-18T, primers specific to the heavy chain and light chain genes of the anti-dengue virus NS1 7D9 antibody were designed, with HindIII and EcoRI restriction sites and protective bases at both ends. The primers were as follows:

```
DN7D9-HF:
                                        (SEQ ID NO: 19)
5'-CCCAAGCTTATGAAGTTGCCTGTTAGGCTGTTGGTGCTGATG-3';

DN7D9-HR:
                                        (SEQ ID NO: 20)
5'-CACGAATTCTTACTAACACTCATTCCTGTTGAAGCTCTTGACAATG-
3';

DN7D9-LF:
                                        (SEQ ID NO: 21)
5'-CATGAAGCTTATGAAGTTGCCTGTTAGGCTGTTGGTGCTGATG-3';

DN7D9-LR:
                                        (SEQ ID NO: 22)
5'-CATGGAATTCTTACTAACACTCATTCCTGTTGAAGCTCTTGACA-
3'.
```

A light chain gene fragment in size of 0.72 KB and a heavy chain gene fragment in size of 1.4 KB were amplified by PCR amplification. The heavy chain and light chain gene fragments were each double digested by HindIII/EcoRI. The 3.4 vector was also double digested by HindIII/EcoRI. After the digested fragments and the vector were purified and recovered, the heavy chain gene and the light chain gene were respectively linked to the 3.4A expression vector, obtaining recombinant expression plasmids for the heavy chain and for the light chain respectively.

Example 2

1. Activity Identification of Binding Protein in the Expression Supernatant

The plasmid was diluted to 400 ng/ml with ultrapure water. Chinese hamster ovary (CHO) cells were adjusted at $1.43\times10^7$ cells/mL in a centrifuge tube. After 100 μL of the plasmid was mixed with 700 μL of the cells, the mixture was transferred into an electroporation cuvette for electrotransformation and then transferred to 10 mL CD CHO AGT medium, which was cultured in a shaker at 37° C. (8% $CO_2$, amplitude 150). The medium was sampled every day for testing the cell viability. Once the cell viability was less than 50%, the cell culture was centrifuged, and the protein sample was obtained in the supernatant.

Antigen DN-II-Ag #(from Fapon Biotech InC.) was diluted 1000-fold with CB. The sample was added to the polystyrene ELISA block at 100 μL per well and left overnight at 4° C. The next day, the ELISA block was washed twice with the wash solution PBST and tapped for drying. The blocking solution (20% BSA+80% PBS) was added at 120 μL per well and left for 1 h at 37° C., and the ELISA block was tapped for drying. The diluted cell supernatant was added at 100 μL per well and left for 30 min (1 h for some supernatant) at 37° C.; then the ELISA block was washed 5 times with the wash solution and tapped for drying. The goat anti-mouse IgG-HRP was added at 100 μL per well and left for 30 min at 37° C.; then the ELISA block was washed 5 times with the wash solution and tapped for drying. Colour-developing solution A was added at 50 μL per well, followed by colour-developing solution B at 50 μL per well and the mixed solution was left for 10 min; and stopping solution was added at 50 μL per well. The OD value was read out at 450 nm (reference at 630 nm) on the microplate reader.

2. Purification of Binding Protein

The above samples were subjected to affinity purification in a protein A affinity chromatography column. After purification, 500 mg of the recombinant antibody was obtained. 4 μg of the purified antibody was taken for reduced SDS-PAGE. Two bands, one of which was a 28 KD light chain (having a sequence as set forth in SEQ ID NO: 11), and the other was a 50 KD heavy chain (having a sequence as set forth in SEQ ID NO: 12), were shown after reduced SDS-PAGE.

3. Antibody Affinity Determination

Using the AMC sensor, the purified antibody was diluted with PBST to 10 μg/ml, and the DN-II quality control recombinant protein (produced by Fapon Biotech InC.) was serially diluted with PBST to 500 nmol/ml, 250 nmol/ml, 125 nmol/ml, 62.5 nmol/ml, 31.3 nmol/ml, 15.6 nmol/ml, 7.81 nmol/ml, and 0 nmol/ml.

Running process was as follows: equilibrating in buffer 1 (PBST) for 60s, immobilizing the antibody in the antibody solution for 300s, incubating in buffer 2 (PBST) for 180s, binding in the antigen solution for 420s, dissociating in the buffer 2 for 1200s, regenerating the sensor with 10 mM GLY solution at pH 1.69 and buffer 3, and outputting the data (KD stands for equilibrium dissociation constant, used to measure affinity; kon stands for binding rate; koff stands for dissociation rate).

Example 3

Although the antibody obtained in Example 2 (with the light chain and heavy chain as set forth in SEQ ID NO: 11 and 12, respectively) could bind to the NS1 protein, its affinity and activity were unsatisfactory. Therefore, mutation is introduced into the light chain CDR and heavy chain CDR of the antibody by the applicant.

In analysis, the complementarity determining regions of the heavy chain was showed as follows:

a CDR1-VH having a sequence of A-S-G-Y-T (X1)-F-T-G-F (X2)-Y-M-H;

a CDR2-VH having a sequence of R-V-N-P-Q (X1)-N-G-G-S(X2)-S-Y-N-Q-K-F-V (X3)-G;

a CDR3-VH having a sequence of A-Q (X1)-E-G-V (X2)-H-Y-D-R-A;

the complementarity determining regions of the light chain was showed as follows:

a CDR1-VL having a sequence of Q-S-L-L-Y-S(X1)-S-N-N(X2)-K-N-S-L-A;

a CDR2-VL having a sequence of W-A-S-T-Q (X1)-E-S;

a CDR3-VL having a sequence of Q-Q-Y-F (X1)-T-Y-A (X2)-Y-T, wherein X1, X2, and X3 are all mutation sites.

After the mutation, antibody activity was detected according to the method provided in Example 2, and some of the results were as follows:

TABLE 1

Mutation sites related to antibody activity

| Site | CDR-VH1 X1 | CDR-VH2 X2/X3 | CDR-VL1 X2 | CDR-VL3 X2 |
|---|---|---|---|---|
| WT | T | S/V | N | A |
| Mutation 1 | S | T/I | Q | P |
| Mutation 2 | S | T/F | H | G |
| Mutation 3 | L | K/H | V | Q |
| Mutation 4 | R | E/A | I | V |
| Mutation 5 | C | R/Q | P | T |

TABLE 2

Antibody activity analysis data

| | WT | Mutation 1 | Mutation 2 | Mutation 3 | Mutation 4 | Mutation 5 |
|---|---|---|---|---|---|---|
| Original | 2.279 | 2.488 | 2.382 | 1.575 | 1.135 | — |
| 3-fold dilution | 2.228 | 2.376 | 2.253 | 0.924 | 0.422 | — |
| 9-fold dilution | 2.372 | 2.463 | 2.337 | 0.312 | 0.059 | — |
| 27-fold dilution | 2.304 | 2.547 | 2.452 | 0.011 | — | — |
| 81-fold dilution | 2.150 | 2.486 | 2.389 | — | — | — |
| 243-fold dilution | 1.013 | 1.763 | 1.601 | — | — | — |
| 729-fold dilution | 0.438 | 0.787 | 0.702 | | | |
| Blank | 0.127 | 0.169 | 0.092 | — | — | — |

"—" means no activity.

It can be seen from the above table that Mutation 1 had the best activity effect, thus Mutation 1 was used as the backbone sequence for screening for mutation sites with better potency. Some of the results were as follows.

TABLE 3

Mutation sites related to antibody affinity

| Site | CDR-VH1 X2 | CDR-VH2 X1 | CDR-VH3 X1/X2 | CDR-VL1 X1 | CDR-VL2 X1 | CDR-VL3 X1 |
|---|---|---|---|---|---|---|
| Mutation 1 | F | Q | Q/V | S | Q | F |
| Mutation 1-1 | Y | D | Q/F | T | R | Y |
| Mutation 1-2 | L | N | Q/Y | S | N | V |
| Mutation 1-3 | F | Q | N/V | T | Q | F |
| Mutation 1-4 | Y | D | N/F | S | R | Y |
| Mutation 1-5 | L | N | N/Y | T | N | V |
| Mutation 1-6 | F | Q | R/V | S | Q | F |
| Mutation 1-7 | Y | D | R/F | T | R | Y |
| Mutation 1-8 | L | N | R/Y | S | N | V |
| Mutation 1-9 | F | D | Q/V | T | Q | F |
| Mutation 1-10 | Y | N | Q/F | S | R | Y |
| Mutation 1-11 | L | Q | Q/Y | T | N | V |
| Mutation 1-12 | F | D | N/V | S | Q | F |
| Mutation 1-13 | Y | N | N/F | T | R | Y |

TABLE 3-continued

| Mutation sites related to antibody affinity | | | | | | |
|---|---|---|---|---|---|---|
| Site | CDR-VH1 X2 | CDR-VH2 X1 | CDR-VH3 X1/X2 | CDR-VL1 X1 | CDR-VL2 X1 | CDR-VL3 X1 |
| Mutation 1-14 | L | Q | N/Y | S | N | V |
| Mutation 1-15 | F | D | R/V | T | Q | F |
| Mutation 1-16 | Y | N | R/F | S | R | Y |
| Mutation 1-17 | L | Q | R/Y | T | N | V |
| Mutation 1-18 | F | D | Q/F | S | R | F |
| Mutation 1-19 | Y | N | Q/Y | T | N | Y |
| Mutation 1-20 | L | Q | N/V | S | Q | V |
| Mutation 1-21 | F | Q | N/F | T | R | F |
| Mutation 1-22 | Y | D | Q/F | S | N | Y |
| Mutation 1-23 | L | N | Q/Y | T | Q | V |
| Mutation 1-24 | F | Q | N/V | S | N | F |
| Mutation 1-25 | Y | Q | N/F | T | Q | F |
| Mutation 1-26 | L | D | Q/Y | S | R | Y |
| Mutation 1-27 | F | N | N/V | T | N | V |
| Mutation 1-28 | Y | Q | N/F | S | N | F |
| Mutation 1-29 | L | D | N/Y | T | Q | Y |
| Mutation 1-30 | F | N | Q/Y | S | R | V |
| Mutation 1-31 | Y | Q | N/V | T | N | V |
| Mutation 1-32 | L | D | N/F | S | Q | F |
| Mutation 1-33 | F | D | N/Y | T | R | Y |
| Mutation 1-34 | Y | N | N/V | S | N | V |
| Mutation 1-35 | L | Q | N/F | T | Q | F |
| Mutation 1-36 | F | D | N/Y | S | Q | Y |
| Mutation 1-37 | Y | N | R/V | T | R | V |
| Mutation 1-38 | L | Q | N/F | S | N | F |
| Mutation 1-39 | F | D | N/Y | S | Q | F |
| Mutation 1-40 | Y | N | R/V | S | R | V |

TABLE 4

| Affinity analysis data | | | |
|---|---|---|---|
| | KD(M) | Kon(1/Ms) | Koff(1/S) |
| Mutation 1 | 3.77E−09 | 4.18E+04 | 1.58E−04 |
| Mutation 1-1 | 5.34E−10 | 4.45E+05 | 2.38E−04 |
| Mutation 1-2 | 7.05E−10 | 4.24E+05 | 2.99E−04 |
| Mutation 1-3 | 3.13E−10 | 4.81E+05 | 1.51E−04 |
| Mutation 1-4 | 2.58E−09 | 4.03E+04 | 1.04E−04 |
| Mutation 1-5 | 5.20E−10 | 4.06E+05 | 2.11E−04 |
| Mutation 1-6 | 6.65E−10 | 4.09E+05 | 2.72E−04 |
| Mutation 1-7 | 8.11E−10 | 4.82E+05 | 3.91E−04 |
| Mutation 1-8 | 4.92E−10 | 4.73E+05 | 2.33E−04 |
| Mutation 1-9 | 2.94E−09 | 4.58E+04 | 1.35E−04 |
| Mutation 1-10 | 4.02E−10 | 4.83E+05 | 1.94E−04 |
| Mutation 1-11 | 4.25E−10 | 4.14E+05 | 1.76E−04 |
| Mutation 1-12 | 2.32E−09 | 4.88E+04 | 1.13E−04 |
| Mutation 1-13 | 3.54E−09 | 4.01E+04 | 1.42E−04 |
| Mutation 1-14 | 2.44E−09 | 4.75E+04 | 1.16E−04 |
| Mutation 1-15 | 3.61E−09 | 4.35E+04 | 1.57E−04 |
| Mutation 1-16 | 3.40E−09 | 4.47E+04 | 1.52E−04 |
| Mutation 1-17 | 3.08E−09 | 4.13E+04 | 1.27E−04 |
| Mutation 1-18 | 3.70E−09 | 4.68E+04 | 1.73E−04 |
| Mutation 1-19 | 2.49E−09 | 4.38E+04 | 1.09E−04 |
| Mutation 1-20 | 2.61E−09 | 4.67E+04 | 1.22E−04 |
| Mutation 1-21 | 2.41E−09 | 4.44E+04 | 1.07E−04 |
| Mutation 1-22 | 3.29E−09 | 4.96E+04 | 1.63E−04 |
| Mutation 1-23 | 3.71E−09 | 4.58E+04 | 1.70E−04 |
| Mutation 1-24 | 4.45E−10 | 4.18E+05 | 1.86E−04 |
| Mutation 1-25 | 2.81E−09 | 4.16E+04 | 1.17E−04 |
| Mutation 1-26 | 3.13E−09 | 4.35E+04 | 1.36E−04 |
| Mutation 1-27 | 3.11E−09 | 4.86E+04 | 1.51E−04 |
| Mutation 1-28 | 4.06E−10 | 4.56E+05 | 1.85E−04 |
| Mutation 1-29 | 3.56E−09 | 4.81E+04 | 1.71E−04 |
| Mutation 1-30 | 3.80E−09 | 4.18E+04 | 1.59E−04 |
| Mutation 1-31 | 2.31E−09 | 4.90E+04 | 1.13E−04 |
| Mutation 1-32 | 3.76E−09 | 4.12E+04 | 1.55E−04 |
| Mutation 1-33 | 3.07E−09 | 4.49E+04 | 1.38E−04 |
| Mutation 1-34 | 2.81E−09 | 4.77E+04 | 1.34E−04 |
| Mutation 1-35 | 2.24E−09 | 4.90E+04 | 1.10E−04 |
| Mutation 1-36 | 2.95E−09 | 4.58E+04 | 1.35E−04 |

TABLE 4-continued

| Affinity analysis data | | | |
|---|---|---|---|
| | KD(M) | Kon(1/Ms) | Koff(1/S) |
| Mutation 1-37 | 3.61E−09 | 4.71E+04 | 1.70E−04 |
| Mutation 1-38 | 2.28E−09 | 4.95E+04 | 1.13E−04 |
| Mutation 1-39 | 3.10E−09 | 4.74E+04 | 1.47E−04 |
| Mutation 1-40 | 3.90E−09 | 4.21E+04 | 1.64E−04 |

The above experiments were repeated with WT as the backbone sequence to verify the affinity of the mutation site. Some of the results are as follows.

TABLE 5

| Mutations with WT as the backbone | | | | | | |
|---|---|---|---|---|---|---|
| Site | CDR-VH1 X2 | CDR-VH2 X1 | CDR-VH3 X1/X2 | CDR-VL1 X1 | CDR-VL2 X1 | CDR-VL3 X1 |
| WT | F | Q | Q/V | S | Q | F |
| WT 1-1 | Y | D | Q/F | T | R | Y |
| WT 1-5 | L | N | Q/Y | S | N | V |
| WT 1-6 | F | Q | N/V | T | Q | F |
| WT 1-11 | Y | D | N/F | S | R | Y |

TABLE 6

| Affinity analysis data | | | |
|---|---|---|---|
| | KD(M) | Kon(1/Ms) | Koff(1/S) |
| WT | 3.93E−08 | 4.12E+03 | 1.62E−04 |
| WT 1-1 | 5.99E−08 | 4.86E+03 | 2.91E−04 |
| WT 1-5 | 6.12E−08 | 4.77E+03 | 2.92E−04 |
| WT 1-6 | 2.98E−08 | 4.92E+03 | 1.46E−04 |
| WT 1-11 | 2.42E−08 | 4.67E+03 | 1.13E−04 |

From the above data analysis, in overall, the antibodies based on Mutation 1 has a higher affinity than that based on WT, provided that the antibody activity is guaranteed.

Example 4

The above self-produced antibodies were stored at 4° C. (in a refrigerator), −80° C. (in a refrigerator), 37° C. (in an incubator) for 21 days. The antibodies were sampled on days 7, 14, and 21 for state observation, and the sample on day 21 was tested for activity. The results showed that there was no significant change in protein status under the three assessment conditions after the antibody was left for 21 days and no decreased activity with the rise of the assessment temperature, indicating that the self-produced antibodies have good stability. The following table shows the OD results from enzyme immunoassay on day 21.

TABLE 7

| Antibody stability assessment | | | |
|---|---|---|---|
| Concentration of Sample (ug/ml) | 3 | 0.75 | 0 |
| Sample on day 21 at 4° C. | 1.518 | 0.665 | 0.019 |
| Sample on day 21 at −80° C. | 1.647 | 0.599 | 0.026 |
| Sample on day 21 at 37° C. | 1.626 | 0.682 | 0.032 |

Finally, it should be noted that the above embodiments are only used for illustration, but not to limit, the technical solutions of the present disclosure. Although the present disclosure has been described in detail with reference to the foregoing embodiments, those of ordinary skill in the art should understand that it is still possible to modify the technical solutions described in the foregoing embodiments, or equivalently replace some or all of the technical features; however, these modifications or replacements do not cause the essence of the corresponding technical solutions to depart from the scope of the technical solutions of the embodiments of the present disclosure.

INDUSTRIAL APPLICABILITY

The isolated binding protein comprising an antigen-binding domain that binds to NS1 protein provided in the present disclosure includes specific heavy chain CDRs and light chain CDRs. The binding protein can specifically recognize and bind to the NS1 protein and has high sensitivity and specificity, thereby enabling detection of dengue fever virus. Moreover, the binding protein may be produced without the mouse abdominal cavity for inducing hybridoma cells, making less difficulty in production and more stable antibody function.

What is claimed is:

1. An antibody against dengue virus NS1 protein comprising an antigen-binding domain, wherein the antigen-binding domain comprises complementarity determining regions CDR1-VH, CDR2-VH, CDR3-VH, CDR1-VL, CDR2-VL, and CDR3-VL as follows:

CDR1-VH consisting of a sequence of A-S-G-Y-X1-F-T-G-X2-Y-M-H (SEQ ID NO: 23), where X1 is S, and X2 is F, Y or L, wherein the CDR1-VH corresponds to positions 24 to 35 of the heavy chain when identified according to the Kabat numbering scheme;

CDR2-VH consisting of a sequence of R-V-N-P-X1-N-G-G-X2-S-Y-N-Q-K-F-X3-G (SEQ ID NO: 24), where X1 is Q, D or N, X2 is T, and X3 is I, wherein the CDR2-VH corresponds to positions 50 to 65 of the heavy chain when identified according to the Kabat numbering scheme;

CDR3-VH consisting of a sequence of A-X1-E-G-X2-H-Y-D-R-A (SEQ ID NO: 25), where X1 is Q, N or R, and X2 is V, F or Y, wherein the CDR3-VH corresponds to positions 93 to 100B of the heavy chain when identified according to the Kabat numbering scheme;

CDR1-VL consisting of a sequence of Q-S-L-L-Y-X1-S-N-X2-K-N-S-L-A (SEQ ID NO: 26), where X1 is S or T, and X2 is-N, Q- or H, wherein the CDR1-VL corresponds to positions 27 to 34 of the light chain when identified according to the Kabat numbering scheme;

CDR2-VL consisting of a sequence of W-A-S-T-X1-E-S (SEQ ID NO: 27), where X1 is Q, R or N, wherein the CDR2-VL corresponds to positions 50 to 56 of the light chain when identified according to the Kabat numbering scheme; and CDR3-VL consisting of a sequence of Q-Q-Y-X1-T-Y-X2-Y-T (SEQ ID NO: 28), where X1 is F, Y or V, and X2 is P, wherein the CDR3-VL corresponds to positions 89 to 97 of the light chain when identified according to the Kabat numbering scheme, and wherein amino acids at corresponding sites of the complementarity determining regions are shown as follows:

| Site | CDR-VH1 X2 | CDR-VH2 X1 | CDR-VH3 X1/X2 | CDR-VL1 X1 | CDR-VL2 X1 | CDR-VL3 X1 |
|---|---|---|---|---|---|---|
| Mutation 1 | F | Q | Q/V | S | Q | F |
| Mutation 1-1 | Y | D | Q/F | T | R | Y |
| Mutation 1-2 | L | N | Q/Y | S | N | V |
| Mutation 1-3 | F | Q | N/V | T | Q | F |
| Mutation 1-4 | Y | D | N/F | S | R | Y |
| Mutation 1-5 | L | N | N/Y | T | N | V |
| Mutation 1-6 | F | Q | R/V | S | Q | F |
| Mutation 1-7 | Y | D | R/F | T | R | Y |
| Mutation 1-8 | L | N | R/Y | S | N | V |
| Mutation 1-9 | F | D | Q/V | T | Q | F |
| Mutation 1-10 | Y | N | Q/F | S | R | Y |
| Mutation 1-11 | L | Q | Q/Y | T | N | V |
| Mutation 1-12 | F | D | N/V | S | Q | F |
| Mutation 1-13 | Y | N | N/F | T | R | Y |
| Mutation 1-14 | L | Q | N/Y | S | N | V |
| Mutation 1-15 | F | D | R/V | T | Q | F |
| Mutation 1-16 | Y | N | R/F | S | R | Y |
| Mutation 1-17 | L | Q | R/Y | T | N | V |
| Mutation 1-18 | F | D | Q/F | S | R | F |
| Mutation 1-19 | Y | N | Q/Y | T | N | Y |
| Mutation 1-20 | L | Q | N/V | S | Q | V |
| Mutation 1-21 | F | Q | N/F | T | R | F |
| Mutation 1-22 | Y | D | Q/F | S | N | Y |
| Mutation 1-23 | L | N | Q/Y | T | Q | V |
| Mutation 1-24 | F | Q | N/V | S | N | F |
| Mutation 1-25 | Y | Q | N/F | T | Q | F |

-continued

| Site | CDR-VH1 X2 | CDR-VH2 X1 | CDR-VH3 X1/X2 | CDR-VL1 X1 | CDR-VL2 X1 | CDR-VL3 X1 |
|---|---|---|---|---|---|---|
| Mutation 1-26 | L | D | Q/Y | S | R | Y |
| Mutation 1-27 | F | N | N/V | T | N | V |
| Mutation 1-28 | Y | Q | N/F | S | N | F |
| Mutation 1-29 | L | D | N/Y | T | Q | Y |
| Mutation 1-30 | F | N | Q/Y | S | R | V |
| Mutation 1-31 | Y | Q | N/V | T | N | V |
| Mutation 1-32 | L | D | N/F | S | Q | F |
| Mutation 1-33 | F | D | N/Y | T | R | Y |
| Mutation 1-34 | Y | N | N/V | S | N | V |
| Mutation 1-35 | L | Q | N/F | T | Q | F |
| Mutation 1-36 | F | D | N/Y | S | Q | Y |
| Mutation 1-37 | Y | N | R/V | T | R | V |
| Mutation 1-38 | L | Q | N/F | S | N | F |
| Mutation 1-39 | F | D | N/Y | S | Q | F |
| Mutation 1-40 | Y | N | R/V | S | R | V. |

2. The antibody according to claim 1, wherein the antibody further comprises a constant region sequence of an antibody.

3. A nucleic acid encoding the antibody according to claim 1.

4. A vector comprising the nucleic acid according to claim 3.

5. An isolated host cell comprising the nucleic acid according to claim 3.

6. A kit comprising the antibody according to claim 1.

7. A method for producing the antibody according to claim 1, comprising culturing an isolated host cell comprising a nucleic acid encoding the antibody according to claim 1 in a culture medium, and recovering the antibody thus produced from the culture medium or from cultured host cell.

8. A method for detecting an dengue virus NS1 protein antigen in a test sample comprising:

A) contacting the dengue virus NS1 protein antigen in the test sample with the antibody according to claim 1 under a condition sufficient for the occurrence of antibody/antigen binding reaction, to form an immune complex; and B) detecting the presence of the immune complex, the presence of the complex indicating the presence of the dengue virus NS1 protein antigen in the test sample.

9. The method according to claim 8, wherein the method is based on fluorescence immunoassay, chemiluminescence immunoassay, immunochromatography, radioimmunoassay and/or enzyme-linked immunoassay.

10. The method according to claim 8, wherein the subject is a mammal.

11. The antibody according to claim 1, wherein the antibody is labelable with an indicator for showing signal intensity.

12. The antibody according to claim 1, wherein the antibody is one of $F(ab')_2$, Fab', Fab, Fv, scFv, or bispecific antibody.

13. The antibody according to claim 1, wherein the antibody comprises light chain framework regions VL-FR1, VL-FR2, VL-FR3 and VL-FR4 having sequences as set forth in SEQ ID NO: 1 to 4, respectively, and/or heavy chain framework regions VH-FR1, VH-FR2, VH-FR3 and VH-FR4 having sequences as set forth in SEQ ID NO: 5 to 8, respectively.

14. The antibody according to claim 2, wherein the constant region sequence is a sequence of a constant region of any one selected from the group consisting of IgG1, IgG2, IgG3, IgG4, IgA, IgM, IgE, and IgD.

15. The antibody according to claim 14, wherein the constant region is derived from species: cattle, horse, dairy cow, pig, sheep, goat, rat, mouse, dog, cat, rabbit, camel, donkey, deer, mink, chicken, duck, goose, turkey, gamecock, or human.

16. The antibody according to claim 15, wherein the constant region is derived from mouse.

17. The antibody according to claim 16, wherein the constant region comprises a light chain constant region having a sequence of SEQ ID NO: 9; and a heavy chain constant region having a sequence of SEQ ID NO: 10.

* * * * *

SEQUENCE LISTING

```
<160> NUMBER OF SEQ ID NOS: 55

<210> SEQ ID NO 1
<211> LENGTH: 26
<212> TYPE: PRT
<213> ORGANISM: Artificial sequence
<220> FEATURE:
<223> OTHER INFORMATION: Light chain framework region FR-L1

<400> SEQUENCE: 1

Asp Ile Val Met Ser Gln Ser Pro Ser Ser Leu Thr Val Ser Val Gly
1               5                   10                  15

Glu Lys Val Thr Met Ser Cys Lys Ser Ser
            20                  25


<210> SEQ ID NO 2
<211> LENGTH: 15
<212> TYPE: PRT
<213> ORGANISM: Artificial Sequence
<220> FEATURE:
<223> OTHER INFORMATION: Light chain framework region FR-L2

<400> SEQUENCE: 2

Trp Tyr Gln Gln Lys Pro Gly Gln Ser Pro Lys Leu Leu Ile Tyr
1               5                   10                  15


<210> SEQ ID NO 3
<211> LENGTH: 32
<212> TYPE: PRT
<213> ORGANISM: Artificial Sequence
<220> FEATURE:
<223> OTHER INFORMATION: Light chain framework region FR-L3

<400> SEQUENCE: 3

Gly Val Pro Asp Arg Phe Thr Gly Ser Gly Ser Gly Thr Asp Phe Thr
1               5                   10                  15

Leu Thr Ile Ser Ser Leu Lys Ala Glu Asp Leu Ala Val Tyr Tyr Cys
            20                  25                  30


<210> SEQ ID NO 4
<211> LENGTH: 10
<212> TYPE: PRT
<213> ORGANISM: Artificial Sequence
<220> FEATURE:
<223> OTHER INFORMATION: Light chain framework region FR-L4

<400> SEQUENCE: 4

Phe Gly Gly Gly Thr Lys Leu Glu Ile Lys
1               5                   10


<210> SEQ ID NO 5
<211> LENGTH: 23
```

<212> TYPE: PRT
<213> ORGANISM: Artificial Sequence
<220> FEATURE:
<223> OTHER INFORMATION: Heavy chain framework region FR-H1

<400> SEQUENCE: 5

```
Glu Val Gln Leu Gln Gln Ser Gly Pro Asp Leu Val Lys Pro Gly Ala
1               5                   10                  15

Ser Val Lys Ile Ser Cys Lys
            20
```

<210> SEQ ID NO 6
<211> LENGTH: 14
<212> TYPE: PRT
<213> ORGANISM: Artificial Sequence
<220> FEATURE:
<223> OTHER INFORMATION: Heavy chain framework region FR-H2

<400> SEQUENCE: 6

```
Trp Val Lys Leu Ser His Gly Lys Ser Leu Ala Trp Ile Gly
1               5                   10
```

<210> SEQ ID NO 7
<211> LENGTH: 30
<212> TYPE: PRT
<213> ORGANISM: Artificial Sequence
<220> FEATURE:
<223> OTHER INFORMATION: Heavy chain framework region FR-H3

<400> SEQUENCE: 7

```
Lys Ala Ile Leu Thr Val Asp Lys Ser Ser Ser Thr Ala Tyr Met Glu
1               5                   10                  15

Leu Arg Ser Leu Thr Ser Glu Asp Ser Ala Val Tyr Tyr Cys
            20                  25                  30
```

<210> SEQ ID NO 8
<211> LENGTH: 15
<212> TYPE: PRT
<213> ORGANISM: Artificial Sequence
<220> FEATURE:
<223> OTHER INFORMATION: Heavy chain framework region FR-H4

<400> SEQUENCE: 8

```
Trp Leu Ala Tyr Trp Gly Gln Gly Thr Leu Val Thr Val Ser Ala
1               5                   10                  15
```

<210> SEQ ID NO 9
<211> LENGTH: 107
<212> TYPE: PRT
<213> ORGANISM: Artificial Sequence
<220> FEATURE:
<223> OTHER INFORMATION: Light chain constant region

<400> SEQUENCE: 9

```
Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80
```

```
Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105


<210> SEQ ID NO 10
<211> LENGTH: 323
<212> TYPE: PRT
<213> ORGANISM: Artificial Sequence
<220> FEATURE:
<223> OTHER INFORMATION: Heavy chain constant region

<400> SEQUENCE: 10

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Gln Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Lys Pro Arg Glu Glu Gln Ile Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asn Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly
```

-continued

<210> SEQ ID NO 11
<211> LENGTH: 220
<212> TYPE: PRT
<213> ORGANISM: Artificial Sequence
<220> FEATURE:
<223> OTHER INFORMATION: Light chain

<400> SEQUENCE: 11

```
Asp Ile Val Met Ser Gln Ser Pro Ser Ser Leu Thr Val Ser Val Gly
1               5                   10                  15

Glu Lys Val Thr Met Ser Cys Lys Ser Ser Gln Ser Leu Leu Tyr Thr
            20                  25                  30

Ser Asn His Lys Asn Ser Leu Ala Trp Tyr Gln Gln Lys Pro Gly Gln
        35                  40                  45

Ser Pro Lys Leu Leu Ile Tyr Trp Ala Ser Thr Gln Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Leu Lys Ala Glu Asp Leu Ala Val Tyr Tyr Cys Gln Gln
                85                  90                  95

Tyr Val Thr Tyr Gly Tyr Thr Phe Gly Gly Gly Thr Lys Leu Glu Ile
            100                 105                 110

Lys Arg Ala Asp Ala Ala Pro Thr Val Ser Ile Phe Pro Pro Ser Ser
        115                 120                 125

Glu Gln Leu Thr Ser Gly Gly Ala Ser Val Val Cys Phe Leu Asn Asn
    130                 135                 140

Phe Tyr Pro Lys Asp Ile Asn Val Lys Trp Lys Ile Asp Gly Ser Glu
145                 150                 155                 160

Arg Gln Asn Gly Val Leu Asn Ser Trp Thr Asp Gln Asp Ser Lys Asp
                165                 170                 175

Ser Thr Tyr Ser Met Ser Ser Thr Leu Thr Leu Thr Lys Asp Glu Tyr
            180                 185                 190

Glu Arg His Asn Ser Tyr Thr Cys Glu Ala Thr His Lys Thr Ser Thr
        195                 200                 205

Ser Pro Ile Val Lys Ser Phe Asn Arg Asn Glu Cys
    210                 215                 220
```

<210> SEQ ID NO 12
<211> LENGTH: 444
<212> TYPE: PRT
<213> ORGANISM: Artificial Sequence
<220> FEATURE:
<223> OTHER INFORMATION: Heavy chain

<400> SEQUENCE: 12

```
Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Leu
            20                  25                  30

Tyr Met His Trp Val Lys Leu Ser His Gly Lys Ser Leu Ala Trp Ile
        35                  40                  45

Gly Arg Val Asn Pro Gln Asn Gly Gly Thr Ser Tyr Asn Gln Lys Phe
    50                  55                  60

Phe Gly Lys Ala Ile Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95
```

-continued

```
Ala Gln Glu Gly Tyr His Tyr Asp Arg Ala Trp Leu Ala Tyr Trp Gly
            100                 105                 110

Gln Gly Thr Leu Val Thr Val Ser Ala Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Gln Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Lys
        275                 280                 285

Pro Arg Glu Glu Gln Ile Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asn Phe Phe Pro Glu Asp Ile Thr Val Glu Trp Gln Trp Asn Gly Gln
    370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly
        435                 440
```

<210> SEQ ID NO 13
<211> LENGTH: 25
<212> TYPE: DNA
<213> ORGANISM: Artificial Sequence
<220> FEATURE:
<223> OTHER INFORMATION: SMARTER II A Oligonucleotide
<220> FEATURE:
<221> NAME/KEY: misc_feature
<222> LOCATION: (25)..(25)
<223> OTHER INFORMATION: XXXXX at the 3'-end

<400> SEQUENCE: 13
aagcagtggt atcaacgcag agtac 25

<210> SEQ ID NO 14
<211> LENGTH: 27
<212> TYPE: DNA
<213> ORGANISM: Artificial Sequence
<220> FEATURE:
<223> OTHER INFORMATION: 5'-RACE CDS Primer (5'-CDS)
<220> FEATURE:
<221> NAME/KEY: misc_feature
<222> LOCATION: (26)..(26)
<223> OTHER INFORMATION: v is a, c, or g
<220> FEATURE:
<221> NAME/KEY: misc_feature
<222> LOCATION: (27)..(27)
<223> OTHER INFORMATION: n is a, c, g, or t

<400> SEQUENCE: 14
tttttttttt tttttttttt tttttvn 27

<210> SEQ ID NO 15
<211> LENGTH: 45
<212> TYPE: DNA
<213> ORGANISM: Artificial Sequence
<220> FEATURE:
<223> OTHER INFORMATION: Universal Primer A Mix (UPM)

<400> SEQUENCE: 15
ctaatacgac tcactatagg gcaagcagtg gtatcaacgc agagt 45

<210> SEQ ID NO 16
<211> LENGTH: 23
<212> TYPE: DNA
<213> ORGANISM: Artificial Sequence
<220> FEATURE:
<223> OTHER INFORMATION: Nested-Universal Primer A (NUP)

<400> SEQUENCE: 16
aagcagtggt atcaacgcag agt 23

<210> SEQ ID NO 17
<211> LENGTH: 39
<212> TYPE: DNA
<213> ORGANISM: Artificial Sequence
<220> FEATURE:
<223> OTHER INFORMATION: mkR

<400> SEQUENCE: 17
ttttcctttt gaattcctaa cactcattcc tgttgaagc 39

<210> SEQ ID NO 18
<211> LENGTH: 31
<212> TYPE: DNA
<213> ORGANISM: Artificial Sequence
<220> FEATURE:
<223> OTHER INFORMATION: mHR

<400> SEQUENCE: 18
acactcattc ctgttgaagc tcttgacaat g 31

<210> SEQ ID NO 19
<211> LENGTH: 42
<212> TYPE: DNA
<213> ORGANISM: Artificial Sequence
<220> FEATURE:
<223> OTHER INFORMATION: DN7D9-HF

<400> SEQUENCE: 19
cccaagctta tgaagttgcc tgttaggctg ttggtgctga tg 42

<210> SEQ ID NO 20
<211> LENGTH: 46
<212> TYPE: DNA
<213> ORGANISM: Artificial Sequence
<220> FEATURE:
<223> OTHER INFORMATION: DN7D9-HR

<400> SEQUENCE: 20
cacgaattct tactaacact cattcctgtt gaagctcttg acaatg 46

<210> SEQ ID NO 21
<211> LENGTH: 43
<212> TYPE: DNA
<213> ORGANISM: Artificial Sequence
<220> FEATURE:
<223> OTHER INFORMATION: DN7D9-LF

<400> SEQUENCE: 21
catgaagctt atgaagttgc ctgttaggct gttggtgctg atg 43

<210> SEQ ID NO 22
<211> LENGTH: 44
<212> TYPE: DNA
<213> ORGANISM: Artificial Sequence
<220> FEATURE:
<223> OTHER INFORMATION: DN7D9-LR

<400> SEQUENCE: 22
catggaattc ttactaacac tcattcctgt tgaagctctt gaca 44

<210> SEQ ID NO 23
<211> LENGTH: 12
<212> TYPE: PRT
<213> ORGANISM: Artificial Sequence
<220> FEATURE:
<223> OTHER INFORMATION: CDR-VH1
<220> FEATURE:
<221> NAME/KEY: MISC_FEATURE
<222> LOCATION: (5)..(5)
<223> OTHER INFORMATION: Xaa is S or T
<220> FEATURE:
<221> NAME/KEY: MISC_FEATURE
<222> LOCATION: (9)..(9)
<223> OTHER INFORMATION: Xaa is F or Y or L

<400> SEQUENCE: 23

Ala Ser Gly Tyr Xaa Phe Thr Gly Xaa Tyr Met His
1 5 10

<210> SEQ ID NO 24
<211> LENGTH: 17
<212> TYPE: PRT
<213> ORGANISM: Artificial Sequence
<220> FEATURE:
<223> OTHER INFORMATION: CDR-VH2
<220> FEATURE:
<221> NAME/KEY: MISC_FEATURE
<222> LOCATION: (5)..(5)
<223> OTHER INFORMATION: Xaa is Q or D or N
<220> FEATURE:
<221> NAME/KEY: MISC_FEATURE
<222> LOCATION: (9)..(9)
<223> OTHER INFORMATION: Xaa is S or T
<220> FEATURE:
<221> NAME/KEY: MISC_FEATURE
<222> LOCATION: (16)..(16)
<223> OTHER INFORMATION: Xaa is V or I or F

<400> SEQUENCE: 24

Arg Val Asn Pro Xaa Asn Gly Gly Xaa Ser Tyr Asn Gln Lys Phe Xaa
1 5 10 15

Gly

<210> SEQ ID NO 25
<211> LENGTH: 10
<212> TYPE: PRT
<213> ORGANISM: Artificial Sequence
<220> FEATURE:
<223> OTHER INFORMATION: CDR-VH3
<220> FEATURE:
<221> NAME/KEY: MISC_FEATURE
<222> LOCATION: (2)..(2)
<223> OTHER INFORMATION: Xaa is Q or N or R
<220> FEATURE:
<221> NAME/KEY: MISC_FEATURE
<222> LOCATION: (5)..(5)
<223> OTHER INFORMATION: Xaa is V or F or Y

<400> SEQUENCE: 25

Ala Xaa Glu Gly Xaa His Tyr Asp Arg Ala
1 5 10

<210> SEQ ID NO 26
<211> LENGTH: 14
<212> TYPE: PRT
<213> ORGANISM: Artificial Sequence
<220> FEATURE:
<223> OTHER INFORMATION: CDR-VL1
<220> FEATURE:
<221> NAME/KEY: MISC_FEATURE
<222> LOCATION: (6)..(6)
<223> OTHER INFORMATION: Xaa is S or T
<220> FEATURE:
<221> NAME/KEY: MISC_FEATURE
<222> LOCATION: (9)..(9)
<223> OTHER INFORMATION: Xaa is N or Q or H

<400> SEQUENCE: 26

Gln Ser Leu Leu Tyr Xaa Ser Asn Xaa Lys Asn Ser Leu Ala
1 5 10

<210> SEQ ID NO 27
<211> LENGTH: 7
<212> TYPE: PRT
<213> ORGANISM: Artificial Sequence
<220> FEATURE:
<223> OTHER INFORMATION: CDR-VL2
<220> FEATURE:
<221> NAME/KEY: MISC_FEATURE
<222> LOCATION: (5)..(5)
<223> OTHER INFORMATION: Xaa is Q or R or N

<400> SEQUENCE: 27

Trp Ala Ser Thr Xaa Glu Ser
1 5

<210> SEQ ID NO 28
<211> LENGTH: 9
<212> TYPE: PRT
<213> ORGANISM: Artificial Sequence
<220> FEATURE:
<223> OTHER INFORMATION: CDR-VL3
<220> FEATURE:
<221> NAME/KEY: MISC_FEATURE
<222> LOCATION: (4)..(4)

-continued

<223> OTHER INFORMATION: Xaa is F or Y or V
<220> FEATURE:
<221> NAME/KEY: MISC_FEATURE
<222> LOCATION: (7)..(7)
<223> OTHER INFORMATION: Xaa is A or P or G

<400> SEQUENCE: 28

Gln Gln Tyr Xaa Thr Tyr Xaa Tyr Thr
1               5

<210> SEQ ID NO 29
<211> LENGTH: 12
<212> TYPE: PRT
<213> ORGANISM: Artificial Sequence
<220> FEATURE:
<223> OTHER INFORMATION: CDR-VH1
<220> FEATURE:
<221> NAME/KEY: MISC_FEATURE
<222> LOCATION: (5)..(5)
<223> OTHER INFORMATION: Xaa is S
<220> FEATURE:
<221> NAME/KEY: MISC_FEATURE
<222> LOCATION: (9)..(9)
<223> OTHER INFORMATION: Xaa is F or Y or L

<400> SEQUENCE: 29

Ala Ser Gly Tyr Xaa Phe Thr Gly Xaa Tyr Met His
1               5                   10

<210> SEQ ID NO 30
<211> LENGTH: 17
<212> TYPE: PRT
<213> ORGANISM: Artificial Sequence
<220> FEATURE:
<223> OTHER INFORMATION: CDR-VH2
<220> FEATURE:
<221> NAME/KEY: MISC_FEATURE
<222> LOCATION: (5)..(5)
<223> OTHER INFORMATION: Xaa is Q or D or N
<220> FEATURE:
<221> NAME/KEY: MISC_FEATURE
<222> LOCATION: (9)..(9)
<223> OTHER INFORMATION: Xaa is T
<220> FEATURE:
<221> NAME/KEY: MISC_FEATURE
<222> LOCATION: (16)..(16)
<223> OTHER INFORMATION: Xaa is I

<400> SEQUENCE: 30

Arg Val Asn Pro Xaa Asn Gly Gly Xaa Ser Tyr Asn Gln Lys Phe Xaa
1               5                   10                  15

Gly

<210> SEQ ID NO 31
<211> LENGTH: 14
<212> TYPE: PRT
<213> ORGANISM: Artificial Sequence
<220> FEATURE:
<223> OTHER INFORMATION: CDR-VL1
<220> FEATURE:
<221> NAME/KEY: MISC_FEATURE
<222> LOCATION: (6)..(6)
<223> OTHER INFORMATION: Xaa is S or T
<220> FEATURE:
<221> NAME/KEY: MISC_FEATURE
<222> LOCATION: (9)..(9)
<223> OTHER INFORMATION: Xaa is Q

<400> SEQUENCE: 31

Gln Ser Leu Leu Tyr Xaa Ser Asn Xaa Lys Asn Ser Leu Ala
1               5                   10

-continued

<210> SEQ ID NO 32
<211> LENGTH: 9
<212> TYPE: PRT
<213> ORGANISM: Artificial Sequence
<220> FEATURE:
<223> OTHER INFORMATION: CDR-VL3
<220> FEATURE:
<221> NAME/KEY: MISC_FEATURE
<222> LOCATION: (4)..(4)
<223> OTHER INFORMATION: Xaa is F or Y or V
<220> FEATURE:
<221> NAME/KEY: MISC_FEATURE
<222> LOCATION: (7)..(7)
<223> OTHER INFORMATION: Xaa is P

<400> SEQUENCE: 32

Gln Gln Tyr Xaa Thr Tyr Xaa Tyr Thr
1               5

<210> SEQ ID NO 33
<211> LENGTH: 12
<212> TYPE: PRT
<213> ORGANISM: Artificial Sequence
<220> FEATURE:
<223> OTHER INFORMATION: CDR-VH1
<220> FEATURE:
<221> NAME/KEY: MISC_FEATURE
<222> LOCATION: (5)..(5)
<223> OTHER INFORMATION: Xaa is S or T
<220> FEATURE:
<221> NAME/KEY: MISC_FEATURE
<222> LOCATION: (9)..(9)
<223> OTHER INFORMATION: Xaa is F

<400> SEQUENCE: 33

Ala Ser Gly Tyr Xaa Phe Thr Gly Xaa Tyr Met His
1               5                   10

<210> SEQ ID NO 34
<211> LENGTH: 12
<212> TYPE: PRT
<213> ORGANISM: Artificial Sequence
<220> FEATURE:
<223> OTHER INFORMATION: CDR-VH1
<220> FEATURE:
<221> NAME/KEY: MISC_FEATURE
<222> LOCATION: (5)..(5)
<223> OTHER INFORMATION: Xaa is S or T
<220> FEATURE:
<221> NAME/KEY: MISC_FEATURE
<222> LOCATION: (9)..(9)
<223> OTHER INFORMATION: Xaa is Y

<400> SEQUENCE: 34

Ala Ser Gly Tyr Xaa Phe Thr Gly Xaa Tyr Met His
1               5                   10

<210> SEQ ID NO 35
<211> LENGTH: 12
<212> TYPE: PRT
<213> ORGANISM: Artificial Sequence
<220> FEATURE:
<223> OTHER INFORMATION: CDR-VH1
<220> FEATURE:
<221> NAME/KEY: MISC_FEATURE
<222> LOCATION: (5)..(5)
<223> OTHER INFORMATION: Xaa is S or T
<220> FEATURE:
<221> NAME/KEY: MISC_FEATURE
<222> LOCATION: (9)..(9)
<223> OTHER INFORMATION: Xaa is L

<400> SEQUENCE: 35

Ala Ser Gly Tyr Xaa Phe Thr Gly Xaa Tyr Met His
1 5 10

<210> SEQ ID NO 36
<211> LENGTH: 17
<212> TYPE: PRT
<213> ORGANISM: Artificial Sequence
<220> FEATURE:
<223> OTHER INFORMATION: CDR-VH2
<220> FEATURE:
<221> NAME/KEY: MISC_FEATURE
<222> LOCATION: (5)..(5)
<223> OTHER INFORMATION: Xaa is Q
<220> FEATURE:
<221> NAME/KEY: MISC_FEATURE
<222> LOCATION: (9)..(9)
<223> OTHER INFORMATION: Xaa is S or T
<220> FEATURE:
<221> NAME/KEY: MISC_FEATURE
<222> LOCATION: (16)..(16)
<223> OTHER INFORMATION: Xaa is V or I or F

<400> SEQUENCE: 36

Arg Val Asn Pro Xaa Asn Gly Gly Xaa Ser Tyr Asn Gln Lys Phe Xaa
1 5 10 15

Gly

<210> SEQ ID NO 37
<211> LENGTH: 17
<212> TYPE: PRT
<213> ORGANISM: Artificial Sequence
<220> FEATURE:
<223> OTHER INFORMATION: CDR-VH2
<220> FEATURE:
<221> NAME/KEY: MISC_FEATURE
<222> LOCATION: (5)..(5)
<223> OTHER INFORMATION: Xaa is D
<220> FEATURE:
<221> NAME/KEY: MISC_FEATURE
<222> LOCATION: (9)..(9)
<223> OTHER INFORMATION: Xaa is S or T
<220> FEATURE:
<221> NAME/KEY: MISC_FEATURE
<222> LOCATION: (16)..(16)
<223> OTHER INFORMATION: Xaa is V or I or F

<400> SEQUENCE: 37

Arg Val Asn Pro Xaa Asn Gly Gly Xaa Ser Tyr Asn Gln Lys Phe Xaa
1 5 10 15

Gly

<210> SEQ ID NO 38
<211> LENGTH: 17
<212> TYPE: PRT
<213> ORGANISM: Artificial Sequence
<220> FEATURE:
<223> OTHER INFORMATION: CDR-VH2
<220> FEATURE:
<221> NAME/KEY: MISC_FEATURE
<222> LOCATION: (5)..(5)
<223> OTHER INFORMATION: Xaa is N
<220> FEATURE:
<221> NAME/KEY: MISC_FEATURE
<222> LOCATION: (9)..(9)
<223> OTHER INFORMATION: Xaa is S or T
<220> FEATURE:
<221> NAME/KEY: MISC_FEATURE
<222> LOCATION: (16)..(16)
<223> OTHER INFORMATION: Xaa is V or I or F -continued

<400> SEQUENCE: 38

Arg Val Asn Pro Xaa Asn Gly Gly Xaa Ser Tyr Asn Gln Lys Phe Xaa
1 5 10 15

Gly

<210> SEQ ID NO 39
<211> LENGTH: 10
<212> TYPE: PRT
<213> ORGANISM: Artificial Sequence
<220> FEATURE:
<223> OTHER INFORMATION: CDR-VH3
<220> FEATURE:
<221> NAME/KEY: MISC_FEATURE
<222> LOCATION: (2)..(2)
<223> OTHER INFORMATION: Xaa is Q
<220> FEATURE:
<221> NAME/KEY: MISC_FEATURE
<222> LOCATION: (5)..(5)
<223> OTHER INFORMATION: Xaa is V

<400> SEQUENCE: 39

Ala Xaa Glu Gly Xaa His Tyr Asp Arg Ala
1 5 10

<210> SEQ ID NO 40
<211> LENGTH: 10
<212> TYPE: PRT
<213> ORGANISM: Artificial Sequence
<220> FEATURE:
<223> OTHER INFORMATION: CDR-VH3
<220> FEATURE:
<221> NAME/KEY: MISC_FEATURE
<222> LOCATION: (2)..(2)
<223> OTHER INFORMATION: Xaa is Q
<220> FEATURE:
<221> NAME/KEY: MISC_FEATURE
<222> LOCATION: (5)..(5)
<223> OTHER INFORMATION: Xaa is F

<400> SEQUENCE: 40

Ala Xaa Glu Gly Xaa His Tyr Asp Arg Ala
1 5 10

<210> SEQ ID NO 41
<211> LENGTH: 10
<212> TYPE: PRT
<213> ORGANISM: Artificial Sequence
<220> FEATURE:
<223> OTHER INFORMATION: CDR-VH3
<220> FEATURE:
<221> NAME/KEY: MISC_FEATURE
<222> LOCATION: (2)..(2)
<223> OTHER INFORMATION: Xaa is Q
<220> FEATURE:
<221> NAME/KEY: MISC_FEATURE
<222> LOCATION: (5)..(5)
<223> OTHER INFORMATION: Xaa is Y

<400> SEQUENCE: 41

Ala Xaa Glu Gly Xaa His Tyr Asp Arg Ala
1 5 10

<210> SEQ ID NO 42
<211> LENGTH: 10
<212> TYPE: PRT
<213> ORGANISM: Artificial Sequence
<220> FEATURE:
<223> OTHER INFORMATION: CDR-VH3
<220> FEATURE:

<221> NAME/KEY: MISC_FEATURE
<222> LOCATION: (2)..(2)
<223> OTHER INFORMATION: Xaa is N
<220> FEATURE:
<221> NAME/KEY: MISC_FEATURE
<222> LOCATION: (5)..(5)
<223> OTHER INFORMATION: Xaa is V

<400> SEQUENCE: 42

Ala Xaa Glu Gly Xaa His Tyr Asp Arg Ala
1 5 10

<210> SEQ ID NO 43
<211> LENGTH: 10
<212> TYPE: PRT
<213> ORGANISM: Artificial Sequence
<220> FEATURE:
<223> OTHER INFORMATION: CDR-VH3
<220> FEATURE:
<221> NAME/KEY: MISC_FEATURE
<222> LOCATION: (2)..(2)
<223> OTHER INFORMATION: Xaa is N
<220> FEATURE:
<221> NAME/KEY: MISC_FEATURE
<222> LOCATION: (5)..(5)
<223> OTHER INFORMATION: Xaa is F

<400> SEQUENCE: 43

Ala Xaa Glu Gly Xaa His Tyr Asp Arg Ala
1 5 10

<210> SEQ ID NO 44
<211> LENGTH: 10
<212> TYPE: PRT
<213> ORGANISM: Artificial Sequence
<220> FEATURE:
<223> OTHER INFORMATION: CDR-VH3
<220> FEATURE:
<221> NAME/KEY: MISC_FEATURE
<222> LOCATION: (2)..(2)
<223> OTHER INFORMATION: Xaa is N
<220> FEATURE:
<221> NAME/KEY: MISC_FEATURE
<222> LOCATION: (5)..(5)
<223> OTHER INFORMATION: Xaa is Y

<400> SEQUENCE: 44

Ala Xaa Glu Gly Xaa His Tyr Asp Arg Ala
1 5 10

<210> SEQ ID NO 45
<211> LENGTH: 10
<212> TYPE: PRT
<213> ORGANISM: Artificial Sequence
<220> FEATURE:
<223> OTHER INFORMATION: CDR-VH3
<220> FEATURE:
<221> NAME/KEY: MISC_FEATURE
<222> LOCATION: (2)..(2)
<223> OTHER INFORMATION: Xaa is R
<220> FEATURE:
<221> NAME/KEY: MISC_FEATURE
<222> LOCATION: (5)..(5)
<223> OTHER INFORMATION: Xaa is V

<400> SEQUENCE: 45

Ala Xaa Glu Gly Xaa His Tyr Asp Arg Ala
1 5 10

<210> SEQ ID NO 46
<211> LENGTH: 10

<212> TYPE: PRT
<213> ORGANISM: Artificial Sequence
<220> FEATURE:
<223> OTHER INFORMATION: CDR-VH3
<220> FEATURE:
<221> NAME/KEY: MISC_FEATURE
<222> LOCATION: (2)..(2)
<223> OTHER INFORMATION: Xaa is R
<220> FEATURE:
<221> NAME/KEY: MISC_FEATURE
<222> LOCATION: (5)..(5)
<223> OTHER INFORMATION: Xaa is F

<400> SEQUENCE: 46

Ala Xaa Glu Gly Xaa His Tyr Asp Arg Ala
1               5                   10

<210> SEQ ID NO 47
<211> LENGTH: 10
<212> TYPE: PRT
<213> ORGANISM: Artificial Sequence
<220> FEATURE:
<223> OTHER INFORMATION: CDR-VH3
<220> FEATURE:
<221> NAME/KEY: MISC_FEATURE
<222> LOCATION: (2)..(2)
<223> OTHER INFORMATION: Xaa is R
<220> FEATURE:
<221> NAME/KEY: MISC_FEATURE
<222> LOCATION: (5)..(5)
<223> OTHER INFORMATION: Xaa is Y

<400> SEQUENCE: 47

Ala Xaa Glu Gly Xaa His Tyr Asp Arg Ala
1               5                   10

<210> SEQ ID NO 48
<211> LENGTH: 14
<212> TYPE: PRT
<213> ORGANISM: Artificial Sequence
<220> FEATURE:
<223> OTHER INFORMATION: CDR-VL1
<220> FEATURE:
<221> NAME/KEY: MISC_FEATURE
<222> LOCATION: (6)..(6)
<223> OTHER INFORMATION: Xaa is S
<220> FEATURE:
<221> NAME/KEY: MISC_FEATURE
<222> LOCATION: (9)..(9)
<223> OTHER INFORMATION: Xaa is N or Q or H

<400> SEQUENCE: 48

Gln Ser Leu Leu Tyr Xaa Ser Asn Xaa Lys Asn Ser Leu Ala
1               5                   10

<210> SEQ ID NO 49
<211> LENGTH: 14
<212> TYPE: PRT
<213> ORGANISM: Artificial Sequence
<220> FEATURE:
<223> OTHER INFORMATION: CDR-VL1
<220> FEATURE:
<221> NAME/KEY: MISC_FEATURE
<222> LOCATION: (6)..(6)
<223> OTHER INFORMATION: Xaa is T
<220> FEATURE:
<221> NAME/KEY: MISC_FEATURE
<222> LOCATION: (9)..(9)
<223> OTHER INFORMATION: Xaa is N or Q or H

<400> SEQUENCE: 49

Gln Ser Leu Leu Tyr Xaa Ser Asn Xaa Lys Asn Ser Leu Ala 1 5 10

<210> SEQ ID NO 50
<211> LENGTH: 7
<212> TYPE: PRT
<213> ORGANISM: Artificial Sequence
<220> FEATURE:
<223> OTHER INFORMATION: CDR-VL2
<220> FEATURE:
<221> NAME/KEY: MISC_FEATURE
<222> LOCATION: (5)..(5)
<223> OTHER INFORMATION: Xaa is Q

<400> SEQUENCE: 50

Trp Ala Ser Thr Xaa Glu Ser
1 5

<210> SEQ ID NO 51
<211> LENGTH: 7
<212> TYPE: PRT
<213> ORGANISM: Artificial Sequence
<220> FEATURE:
<223> OTHER INFORMATION: CDR-VL2
<220> FEATURE:
<221> NAME/KEY: MISC_FEATURE
<222> LOCATION: (5)..(5)
<223> OTHER INFORMATION: Xaa is R

<400> SEQUENCE: 51

Trp Ala Ser Thr Xaa Glu Ser
1 5

<210> SEQ ID NO 52
<211> LENGTH: 7
<212> TYPE: PRT
<213> ORGANISM: Artificial Sequence
<220> FEATURE:
<223> OTHER INFORMATION: CDR-VL2
<220> FEATURE:
<221> NAME/KEY: MISC_FEATURE
<222> LOCATION: (5)..(5)
<223> OTHER INFORMATION: Xaa is N

<400> SEQUENCE: 52

Trp Ala Ser Thr Xaa Glu Ser
1 5

<210> SEQ ID NO 53
<211> LENGTH: 9
<212> TYPE: PRT
<213> ORGANISM: Artificial Sequence
<220> FEATURE:
<223> OTHER INFORMATION: CDR-VL3
<220> FEATURE:
<221> NAME/KEY: MISC_FEATURE
<222> LOCATION: (4)..(4)
<223> OTHER INFORMATION: Xaa is F
<220> FEATURE:
<221> NAME/KEY: MISC_FEATURE
<222> LOCATION: (7)..(7)
<223> OTHER INFORMATION: Xaa is A or P or G

<400> SEQUENCE: 53

Gln Gln Tyr Xaa Thr Tyr Xaa Tyr Thr
1 5

<210> SEQ ID NO 54
<211> LENGTH: 9
<212> TYPE: PRT
<213> ORGANISM: Artificial Sequence -continued

```
<220> FEATURE:
<223> OTHER INFORMATION: CDR-VL3
<220> FEATURE:
<221> NAME/KEY: MISC_FEATURE
<222> LOCATION: (4)..(4)
<223> OTHER INFORMATION: Xaa is Y
<220> FEATURE:
<221> NAME/KEY: MISC_FEATURE
<222> LOCATION: (7)..(7)
<223> OTHER INFORMATION: Xaa is A or P or G

<400> SEQUENCE: 54

Gln Gln Tyr Xaa Thr Tyr Xaa Tyr Thr
1               5


<210> SEQ ID NO 55
<211> LENGTH: 9
<212> TYPE: PRT
<213> ORGANISM: Artificial Sequence
<220> FEATURE:
<223> OTHER INFORMATION: CDR-VL3
<220> FEATURE:
<221> NAME/KEY: MISC_FEATURE
<222> LOCATION: (4)..(4)
<223> OTHER INFORMATION: Xaa is V
<220> FEATURE:
<221> NAME/KEY: MISC_FEATURE
<222> LOCATION: (7)..(7)
<223> OTHER INFORMATION: Xaa is A or P or G

<400> SEQUENCE: 55

Gln Gln Tyr Xaa Thr Tyr Xaa Tyr Thr
1               5
```